(12) United States Patent
Lopez Muedano et al.

(10) Patent No.: US 12,102,768 B2
(45) Date of Patent: Oct. 1, 2024

(54) BREATHING CIRCUIT COMPONENTS FOR RESPIRATORY APPARATUS

(71) Applicant: Fisher & Paykel Healthcare Limited, Auckland (NZ)

(72) Inventors: Carlos Alberto Lopez Muedano, Auckland (NZ); Nathan Lee Gray, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 401 days.

(21) Appl. No.: 16/307,113

(22) PCT Filed: Jun. 7, 2017

(86) PCT No.: PCT/NZ2017/050074
§ 371 (c)(1),
(2) Date: Dec. 4, 2018

(87) PCT Pub. No.: WO2017/213523
PCT Pub. Date: Dec. 14, 2017

(65) Prior Publication Data
US 2019/0224439 A1     Jul. 25, 2019

Related U.S. Application Data

(60) Provisional application No. 62/346,840, filed on Jun. 7, 2016.

(51) Int. Cl.
*A61M 16/08*     (2006.01)
*A61L 29/06*     (2006.01)
(Continued)

(52) U.S. Cl.
CPC .......... *A61M 16/142* (2014.02); *A61L 29/06* (2013.01); *A61L 29/14* (2013.01);
(Continued)

(58) Field of Classification Search
CPC ............ A61M 16/142; A61M 16/0883; A61M 16/1095; A61M 16/0066; A61M 16/0465;
(Continued)

(56) References Cited

U.S. PATENT DOCUMENTS

| 928,237 A | 7/1909 | Baird |
|---|---|---|
| 2,868,199 A | 1/1959 | Hudson |

(Continued)

FOREIGN PATENT DOCUMENTS

| AU | 200013529 | 6/2000 |
|---|---|---|
| CA | 2833707 | 11/2001 |

(Continued)

OTHER PUBLICATIONS

English translation for JP 2000107104, translated on Jun. 15, 2022 by Search engine through Clarivate Analytics.*

(Continued)

*Primary Examiner* — Tu A Vo
(74) *Attorney, Agent, or Firm* — Knobbe Martens Olson & Bear LLP

(57) ABSTRACT

In one embodiment, a breathing circuit component is provided and includes: an inlet; an outlet; and an enclosing wall defining a gases passageway between the inlet and the outlet, at least a region of the wall comprising a membrane that allows the passage of water vapour without substantially allowing the passage of liquid water or respiratory gases, wherein, the membrane has a thickness of about 35 to 45 micrometers.

20 Claims, 14 Drawing Sheets

(51) Int. Cl.
*A61L 29/14* (2006.01)
*A61M 16/00* (2006.01)
*A61M 16/04* (2006.01)
*A61M 16/06* (2006.01)
*A61M 16/10* (2006.01)
*A61M 16/14* (2006.01)
*A61M 16/16* (2006.01)
*A61M 25/00* (2006.01)
*A61M 39/08* (2006.01)

(52) U.S. Cl.
CPC .... *A61M 16/0066* (2013.01); *A61M 16/0465* (2013.01); *A61M 16/0666* (2013.01); *A61M 16/0816* (2013.01); *A61M 16/0875* (2013.01); *A61M 16/0883* (2014.02); *A61M 16/1095* (2014.02); *A61M 16/16* (2013.01); *A61M 39/08* (2013.01); *A61M 16/04* (2013.01); *A61M 16/06* (2013.01); *A61M 25/0032* (2013.01); *A61M 2205/42* (2013.01); *A61M 2205/7536* (2013.01); *A61M 2209/06* (2013.01)

(58) Field of Classification Search
CPC .......... A61M 16/0666; A61M 16/0816; A61M 16/0875; A61M 16/16; A61M 39/08; A61M 16/04; A61M 16/06; A61M 25/0032; A61M 2205/42; A61M 2205/7536; A61M 2209/06; A61L 29/06; A61L 29/14
See application file for complete search history.

(56) References Cited

U.S. PATENT DOCUMENTS

| | | |
|---|---|---|
| 3,144,313 A | 8/1964 | Pfefferie |
| 3,228,877 A | 1/1966 | Mahon |
| 3,245,206 A | 4/1966 | Bonnet |
| 3,292,346 A | 12/1966 | Adams |
| 3,303,105 A | 2/1967 | Konikoff et al. |
| 3,307,330 A | 3/1967 | Niedzielski et al. |
| 3,367,850 A | 2/1968 | Johnson |
| 3,376,181 A | 4/1968 | Larson et al. |
| 3,394,954 A | 7/1968 | Sarns |
| 3,434,471 A | 3/1969 | Liston |
| 3,513,844 A | 5/1970 | Smith |
| 3,578,777 A | 5/1971 | Degain |
| 3,616,796 A | 11/1971 | Jackson |
| 3,639,970 A | 2/1972 | Larkin |
| 3,682,171 A | 8/1972 | Dali et al. |
| 3,700,513 A | 10/1972 | Haberhauer et al. |
| 3,735,558 A | 5/1973 | Skarstrom et al. |
| 3,735,559 A | 5/1973 | Salemme |
| 3,754,552 A | 8/1973 | King |
| 3,803,810 A | 4/1974 | Rosenberg |
| 3,829,340 A | 8/1974 | Dembiak et al. |
| 3,856,051 A | 12/1974 | Bain |
| 3,858,615 A * | 1/1975 | Weigl .................. F16L 57/02 138/121 |
| 3,871,373 A | 3/1975 | Jackson |
| 3,889,717 A | 6/1975 | Obadal et al. |
| 3,891,556 A | 6/1975 | Ricahrdson et al. |
| 3,895,630 A | 7/1975 | Bachman |
| 3,910,808 A | 10/1975 | Steward |
| 3,912,795 A | 10/1975 | Jackson |
| 3,963,856 A | 6/1976 | Carlson et al. |
| 3,966,525 A | 6/1976 | Steward |
| 4,007,737 A | 2/1977 | Paluch |
| 4,035,211 A | 7/1977 | Bill et al. |
| 4,048,993 A | 9/1977 | Dobritz |
| 4,083,245 A | 4/1978 | Osborn |
| 4,086,035 A | 4/1978 | Klaeger, Jr. et al. |
| 4,130,617 A | 12/1978 | Wallace |
| 4,204,562 A | 5/1980 | Kelly |
| 4,207,457 A | 6/1980 | Haglunc et al. |
| 4,216,769 A | 8/1980 | Grimes |
| 4,262,704 A | 4/1981 | Grawey |
| 4,265,235 A | 5/1981 | Fukunaga |
| 4,265,239 A | 5/1981 | Fischer, Jr. et al. |
| 4,318,398 A | 3/1982 | Oetjen et al. |
| 4,327,718 A | 5/1982 | Cronenberg |
| 4,327,775 A | 5/1982 | Tally |
| 4,336,798 A | 6/1982 | Beran |
| 4,337,800 A | 7/1982 | Carlson et al. |
| 4,343,672 A | 8/1982 | Kanao |
| 4,367,735 A | 1/1983 | Dali |
| 4,368,088 A | 1/1983 | Asakura et al. |
| 4,403,514 A | 9/1983 | Osborn |
| 4,406,283 A | 9/1983 | Bir |
| 4,406,514 A | 9/1983 | Hillegonds et al. |
| 4,409,283 A | 10/1983 | Bir |
| 4,417,574 A | 11/1983 | Talonn et al. |
| 4,420,016 A | 12/1983 | Nichols |
| 4,456,034 A | 6/1984 | Bixby |
| 4,462,397 A | 7/1984 | Suzuki |
| 4,463,755 A | 8/1984 | Suzuki |
| 4,469,495 A | 9/1984 | Hiraizumi et al. |
| 4,490,575 A | 12/1984 | Kutnyak |
| 4,493,870 A | 1/1985 | Vrouenraets et al. |
| 4,509,359 A | 4/1985 | Gedeon et al. |
| 4,580,816 A | 4/1986 | Campbell et al. |
| 4,592,351 A | 6/1986 | Smith et al. |
| 4,597,596 A | 7/1986 | Tozer |
| 4,621,632 A | 11/1986 | Bartels et al. |
| 4,653,542 A | 3/1987 | Tascher |
| 4,682,010 A | 7/1987 | Drapeau et al. |
| 4,686,354 A | 8/1987 | Makin |
| 4,698,196 A | 10/1987 | Fabian |
| 4,698,890 A | 10/1987 | Neaves |
| 4,705,543 A | 11/1987 | Kertzman |
| 4,708,831 A | 11/1987 | Elsworth et al. |
| 4,715,915 A | 12/1987 | Vanderzee |
| 4,722,334 A | 2/1988 | Blackmer et al. |
| 4,753,233 A | 6/1988 | Grimes |
| 4,771,770 A | 9/1988 | Artemenko et al. |
| 4,773,410 A | 9/1988 | Blackmer et al. |
| 4,791,963 A | 12/1988 | Gronert et al. |
| 4,808,201 A | 2/1989 | Kertzman |
| 4,825,863 A | 5/1989 | Dittmar et al. |
| 4,844,719 A | 7/1989 | Toyomoto et al. |
| 4,875,908 A | 10/1989 | Kikukawa et al. |
| 4,886,528 A | 12/1989 | Aaltonen et al. |
| 4,910,384 A | 3/1990 | Silver |
| 4,915,104 A | 4/1990 | Marcy |
| 4,915,105 A | 4/1990 | Lee |
| 4,919,128 A | 4/1990 | Kopala et al. |
| 4,932,269 A | 6/1990 | Cammarata, III et al. |
| 4,938,752 A | 7/1990 | Vrouenraets et al. |
| 4,967,744 A | 11/1990 | Chua |
| 4,985,055 A | 1/1991 | Thorne et al. |
| 4,995,384 A | 2/1991 | Keeling |
| 5,042,500 A | 8/1991 | Norlien et al. |
| 5,044,361 A | 9/1991 | Werner et al. |
| 5,046,531 A | 9/1991 | Kanao |
| 5,088,332 A | 2/1992 | Merilainen et al. |
| 5,160,511 A | 11/1992 | Lovelock |
| 5,165,395 A | 11/1992 | Ricci |
| 5,223,996 A | 6/1993 | Read et al. |
| 5,230,119 A | 7/1993 | Woods et al. |
| 5,233,996 A | 8/1993 | Coleman et al. |
| 5,273,032 A | 12/1993 | Borody |
| 5,284,160 A | 2/1994 | Dryden |
| 5,308,337 A | 5/1994 | Bingisser |
| 5,335,656 A | 8/1994 | Bowe et al. |
| 5,341,206 A | 8/1994 | Pittaro et al. |
| 5,357,948 A | 10/1994 | Eilentropp |
| 5,365,938 A | 11/1994 | Eskela |
| 5,367,604 A | 11/1994 | Murray |
| 5,377,670 A | 1/1995 | Smith |
| 5,392,770 A | 2/1995 | Clawson et al. |
| 5,411,474 A | 5/1995 | Ott et al. |
| 5,427,291 A | 6/1995 | Smith |

(56) References Cited

U.S. PATENT DOCUMENTS

| | | |
|---|---|---|
| 5,438,978 A | 8/1995 | Hardester, III |
| 5,445,874 A | 8/1995 | Shehata |
| 5,445,875 A | 8/1995 | Persson |
| 5,454,061 A | 9/1995 | Carlson |
| 5,461,122 A | 10/1995 | Yilgor et al. |
| 5,462,048 A | 10/1995 | Lambert et al. |
| 5,501,212 A | 3/1996 | Psaros |
| 5,513,634 A | 5/1996 | Jackson |
| 5,532,053 A | 7/1996 | Mueller |
| 5,537,996 A | 7/1996 | Mcphee |
| 5,558,087 A | 9/1996 | Psaros et al. |
| 5,586,551 A | 12/1996 | Hillard |
| 5,595,174 A | 1/1997 | Gwaltney |
| 5,599,610 A | 2/1997 | Levy |
| 5,603,991 A | 2/1997 | Kupiecki et al. |
| 5,611,332 A | 3/1997 | Bono |
| 5,614,588 A | 3/1997 | Steenblock et al. |
| 5,620,500 A | 4/1997 | Fukui et al. |
| 5,623,922 A | 4/1997 | Smith |
| 5,630,409 A | 5/1997 | Bono et al. |
| 5,637,168 A | 6/1997 | Carlson |
| 5,640,951 A | 6/1997 | Huddart et al. |
| 5,645,054 A | 7/1997 | Cotner et al. |
| 5,653,228 A | 8/1997 | Bryd |
| 5,704,344 A | 1/1998 | Cole |
| 5,709,762 A | 1/1998 | Rowan |
| 5,715,647 A | 2/1998 | Keim et al. |
| 5,738,808 A | 4/1998 | Iwamoto |
| 5,769,071 A | 6/1998 | Turnbull |
| 5,794,619 A | 8/1998 | Edelman et al. |
| 5,794,986 A | 8/1998 | Gansel et al. |
| 5,798,013 A | 8/1998 | Brandenburger |
| 5,823,184 A | 10/1998 | Gross |
| 5,848,223 A | 12/1998 | Carlson |
| 5,850,833 A | 12/1998 | Kotliar |
| 5,862,651 A | 1/1999 | Stewart et al. |
| 5,862,652 A | 1/1999 | Schoeler |
| 5,894,839 A | 4/1999 | Rosenkoetter et al. |
| 5,964,219 A | 10/1999 | Pekka |
| 5,975,144 A | 11/1999 | Akedo et al. |
| 5,983,896 A | 11/1999 | Fukunaga et al. |
| 5,992,413 A | 11/1999 | Martin, Jr. et al. |
| 6,029,660 A | 2/2000 | Callauad et al. |
| 6,033,368 A | 3/2000 | Gaston, IV et al. |
| 6,039,696 A | 3/2000 | Bell |
| 6,050,260 A | 4/2000 | Daniell et al. |
| 6,078,730 A | 6/2000 | Huddart et al. |
| 6,098,615 A | 8/2000 | Lloyd et al. |
| 6,105,576 A | 8/2000 | Clawson et al. |
| 6,116,235 A | 9/2000 | Walters et al. |
| 6,119,694 A | 9/2000 | Correa |
| 6,148,818 A | 11/2000 | Pagan |
| 6,167,883 B1 | 1/2001 | Beran et al. |
| 6,192,886 B1 | 2/2001 | Rudolph |
| 6,192,941 B1 | 2/2001 | Mallen-Herrero et al. |
| 6,201,223 B1 | 3/2001 | Nitta |
| 6,272,933 B1 | 8/2001 | Gradon et al. |
| 6,349,722 B1 | 2/2002 | Gradon et al. |
| 6,363,930 B1 | 3/2002 | Clawson et al. |
| 6,367,472 B1 | 4/2002 | Koch |
| 6,367,510 B1 | 4/2002 | Carlson |
| 6,378,520 B1 | 4/2002 | Davenport |
| 6,394,145 B1 | 5/2002 | Bailly |
| 6,412,481 B1 | 7/2002 | Bienvenu et al. |
| 6,427,694 B1 * | 8/2002 | Hecker .............. A61M 16/06 128/206.21 |
| 6,431,172 B1 | 8/2002 | Bordewick |
| 6,432,169 B1 | 8/2002 | Kluwe et al. |
| 6,474,335 B1 | 11/2002 | Lammers |
| 6,516,798 B1 | 2/2003 | Davies |
| 6,523,538 B1 | 2/2003 | Wikefeldt |
| 6,536,136 B2 | 3/2003 | McGlothen |
| 6,536,428 B1 | 3/2003 | Smith et al. |
| 6,536,436 B1 | 3/2003 | McGlothen |
| 6,539,937 B1 | 4/2003 | Havari |
| 6,561,219 B1 | 5/2003 | Apostolides |
| 6,571,794 B1 * | 6/2003 | Hansen ............. A61M 16/0875 138/121 |
| 6,584,972 B2 | 7/2003 | McPhee |
| 6,595,215 B2 | 7/2003 | Wood |
| 6,637,434 B2 | 10/2003 | Noble |
| 6,662,802 B2 | 12/2003 | Smith et al. |
| 6,667,592 B2 | 12/2003 | Jacobs et al. |
| 6,684,883 B1 | 2/2004 | Burns |
| 6,718,973 B2 | 4/2004 | Koch |
| 6,742,399 B2 | 6/2004 | Kunz et al. |
| 6,769,431 B2 | 8/2004 | Smith et al. |
| 6,769,432 B1 | 8/2004 | Keifer |
| 6,779,522 B2 | 8/2004 | Smith et al. |
| 6,807,967 B2 | 10/2004 | Wood |
| 6,986,353 B2 | 1/2006 | Wright |
| 7,140,366 B2 | 11/2006 | Smith et al. |
| 7,469,719 B2 * | 12/2008 | Gray .................. F16L 9/16 138/33 |
| 7,493,902 B2 | 2/2009 | White et al. |
| RE40,806 E | 6/2009 | Gradon et al. |
| 7,559,324 B2 | 7/2009 | Smith |
| 7,900,628 B2 | 3/2011 | Matula et al. |
| 7,905,232 B2 | 3/2011 | Olsen et al. |
| 7,958,891 B2 | 6/2011 | Smith et al. |
| 8,037,882 B2 | 10/2011 | Smith et al. |
| 8,220,463 B2 | 7/2012 | White et al. |
| 8,267,092 B2 | 9/2012 | White et al. |
| 8,851,076 B2 | 10/2014 | White et al. |
| 8,905,082 B2 | 12/2014 | Gray |
| 8,980,036 B2 | 3/2015 | Smith et al. |
| 9,067,035 B2 | 6/2015 | Ophir et al. |
| 9,802,020 B2 | 10/2017 | Smith et al. |
| 9,827,393 B2 | 11/2017 | Smith et al. |
| 9,849,262 B2 | 12/2017 | White et al. |
| 9,878,120 B2 | 1/2018 | White et al. |
| 10,159,814 B2 | 12/2018 | Smith |
| 10,220,175 B2 | 3/2019 | White et al. |
| 10,238,828 B2 | 3/2019 | O'Connor et al. |
| 10,252,017 B2 | 4/2019 | Smith et al. |
| 10,286,174 B2 | 5/2019 | Smith et al. |
| 10,350,376 B2 | 7/2019 | White et al. |
| 2001/0054422 A1 | 12/2001 | Smith et al. |
| 2002/0002976 A1 | 1/2002 | Smith et al. |
| 2002/0046755 A1 | 4/2002 | De Voss |
| 2002/0055685 A1 | 5/2002 | Levitsky et al. |
| 2002/0059935 A1 | 5/2002 | Wood |
| 2002/0195104 A1 | 12/2002 | Fini et al. |
| 2003/0028139 A1 | 2/2003 | Inoue |
| 2003/0047185 A1 | 3/2003 | Olsen et al. |
| 2003/0062048 A1 | 4/2003 | Gradon et al. |
| 2003/0070680 A1 | 4/2003 | Smith et al. |
| 2003/0094178 A1 | 5/2003 | McAuley et al. |
| 2003/0213490 A1 | 11/2003 | Righetti |
| 2004/0081784 A1 * | 4/2004 | Smith .................. B32B 37/26 428/36.9 |
| 2004/0099268 A1 | 5/2004 | Smith et al. |
| 2006/0162726 A1 | 7/2006 | Smith et al. |
| 2007/0235100 A1 | 10/2007 | Tomerlin et al. |
| 2008/0072986 A1 | 3/2008 | Burrowes et al. |
| 2009/0025724 A1 | 1/2009 | Herron, Jr. |
| 2009/0078259 A1 * | 3/2009 | Kooij .................. F16L 3/13 128/205.25 |
| 2009/0088656 A1 | 4/2009 | Levitsky et al. |
| 2009/0126817 A1 | 5/2009 | Gray |
| 2011/0023987 A1 * | 2/2011 | Zucker ............. A61M 16/0875 138/120 |
| 2012/0090622 A1 | 4/2012 | Chang |
| 2013/0098360 A1 * | 4/2013 | Hurmez ............. A61M 16/0057 128/203.12 |
| 2014/0000626 A1 * | 1/2014 | O'Connor ......... A61M 16/0688 128/207.18 |
| 2014/0053939 A1 * | 2/2014 | Kaye .................. F16L 33/34 138/109 |
| 2014/0180157 A1 | 6/2014 | Levitsky et al. |
| 2014/0202462 A1 * | 7/2014 | Stoks ................ A61M 16/0883 128/204.18 |

(56) References Cited

U.S. PATENT DOCUMENTS

| | | | |
|---|---|---|---|
| 2015/0027204 A1* | 1/2015 | Stoks | A61M 16/0841 |
| | | | 73/31.05 |
| 2015/0083125 A1 | 3/2015 | White et al. | |
| 2015/0208953 A1 | 7/2015 | Levitsky et al. | |
| 2015/0306333 A1 | 10/2015 | Amadio et al. | |
| 2016/0045702 A1 | 2/2016 | Milne et al. | |
| 2017/0296769 A1 | 10/2017 | Smith et al. | |
| 2018/0071477 A1 | 3/2018 | Smith et al. | |
| 2018/0071478 A1 | 3/2018 | Smith et al. | |
| 2018/0133428 A1 | 5/2018 | Smith et al. | |
| 2018/0296787 A1* | 10/2018 | Maurer | A61M 16/16 |
| 2019/0201649 A1 | 7/2019 | Smith et al. | |
| 2019/0366028 A1 | 12/2019 | White et al. | |

FOREIGN PATENT DOCUMENTS

| | | | | |
|---|---|---|---|---|
| CA | 2346628 | | 7/2010 | |
| CA | 2697142 | | 2/2014 | |
| DE | 28036 | | 2/1984 | |
| EP | 0535379 | | 4/1993 | |
| EP | 0557040 | | 8/1993 | |
| EP | 0567158 | | 10/1993 | |
| EP | 0621050 | | 10/1994 | |
| EP | 0815792 | | 1/1998 | |
| EP | 0935971 A2 | | 8/1999 | |
| EP | 1014527 | | 6/2000 | |
| EP | 1166814 | | 1/2002 | |
| EP | 0747078 B1 | | 10/2002 | |
| EP | 0885623 B1 | | 11/2004 | |
| EP | 1484161 | | 12/2004 | |
| EP | 1524937 | | 4/2005 | |
| EP | 1477200 | | 10/2006 | |
| EP | 1153627 | | 11/2007 | |
| EP | 1884343 | | 2/2008 | |
| EP | 1885460 | | 2/2008 | |
| EP | 1681071 | | 2/2009 | |
| EP | 2226341 | | 9/2010 | |
| EP | 2305336 | | 4/2011 | |
| EP | 2025359 | | 9/2013 | |
| EP | 2666795 | | 11/2013 | |
| FR | 2638361 | | 5/1990 | |
| GB | 9683 | | 4/1909 | |
| GB | 587163 | | 4/1947 | |
| GB | 1492459 | | 11/1977 | |
| GB | 2024100 | | 1/1980 | |
| GB | 2252515 | | 12/1992 | |
| GB | 2139110 | | 11/1994 | |
| GB | 2284356 A | | 6/1995 | |
| JP | S62-236724 | | 10/1987 | |
| JP | 03-168155 | | 7/1991 | |
| JP | H05-052378 | | 3/1993 | |
| JP | H06-023051 | | 2/1994 | |
| JP | H09-234247 | | 9/1997 | |
| JP | 10248935 | | 9/1998 | |
| JP | 11323899 A | | 11/1999 | |
| JP | 2000-24111 | | 1/2000 | |
| JP | 2000-24113 | | 1/2000 | |
| JP | 2000107104 A | * | 4/2000 | |
| TW | 513318 | | 12/2002 | |
| WO | WO 88/01903 | | 3/1988 | |
| WO | WO 95/16746 | | 6/1995 | |
| WO | WO 95/33163 | | 12/1995 | |
| WO | WO 97/18001 | | 5/1997 | |
| WO | WO 98/02199 | | 1/1998 | |
| WO | WO 98/41148 | | 9/1998 | |
| WO | WO 99/64077 | | 12/1999 | |
| WO | WO 00/48682 | | 8/2000 | |
| WO | WO 01/41854 | | 6/2001 | |
| WO | WO 01/49351 | | 7/2001 | |
| WO | WO 2006/120683 | | 11/2006 | |
| WO | WO 2012/077052 A1 | | 6/2012 | |
| WO | WO-2014182179 A2 | * | 11/2014 | A61M 16/0683 |
| WO | WO-2015025318 A1 | * | 2/2015 | A61M 16/0057 |

OTHER PUBLICATIONS

BS 6151:1992 (ISO 5367:1991), British Standard, Specification for Breathing tubes for use with anaesthetic apparatus and ventilators, in 12 pages.
European Examination Report for European Patent Application 17202695.7 dated Aug. 19, 2020, 4 pages.
R.D. Farley and D.H. Franklin, "Development of a humidifier for patient ventilation using a semi-permeable tube to minimize system condensate," J. Biomed. Eng., vol. 14, Sep. 1992.
MR700, MR720, MR730 Manual, in 48 pages.
Perma Pure Bulletin 104, in 4 pages.
K. Dijkstra Stroeks, "Modeling the moisture vapour transmission rate through segmented block co-poly(ether-ester) based breathable films," Polymer, vol. 42, Issue 1, Jan. 2001, pp. 117-127.
Adams et al; Thermoplastic Polyether Ester Elastomers; Supplied by British Library; unknown date.
MBM-200 Deltatrac II Service Manual; Datex/Division of Instrumentarium Corp; Mar. 1, 1993.
Sparrow; Flow Serparation in a Diversging conical duct: Effect of Reynolds number and divergence angle; International Journal of Heat and Mass Transfer; Jun. 2009.
Gibson; Effect of Temperature on Water Vapor Transport Through Polymer Membrane Laminates; U.S. Army; Feb. 1999.
Gibson; Measurement of water vapor diffusion through laminated fabrics and membranes using a diode laser spectroscope; US Army; Jan. 1998.
Gibson; On the Flow of Water through Pipes and Passages having converging or Diverging Boundaries; Univ. College, Dundee; Oct. 10, 1909.
Gravenstein; Gas Monitoring in Clinical Practice; Butterworth-Heinemann; 1995.
Johnson-Schultze; Breathable TPE Films for Medical Applications; Medical Device & Diagnostic Industry Magazine; Jul. 1, 2000.
Smart Anesthesai Multi-Gas SAM/SAM-80 Module Field Service Manual; Marquette Medical Systems; Mar. 27, 1998.
Flow of Fluids through Valves, Fittings, and Pipe; Crano Co., 1999.
www.permapure.com; capture from archive.org; ME-Series Moisture Exchangers; Perma Pure; Mar. 3, 2001.
www.permapure.com; capture from archive.org; Medical Gas Dryers; Perma Pure; Oct. 17, 2000.
www.permapure.com capture from archive.org; Dryers, Sampling Systems; Perma Pure; Jan. 27, 1999.
Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 17 pages.
Exhibit A, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 34 pages.
Exhibit B, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 16 pages.
Exhibit C, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 31 pages.
Exhibit D, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 15 pages.
Exhibit E, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 16 pages.
Exhibit F, Fisher & Paykel Healthcare Limited's Disclosure of Asserted Claims and Infringement Contentions, *Fisher & Paykel Healthcare Limited v. Flexicare Incorporated*, Case No. 8:19-CV-00835JVS(DFMx), Aug. 19, 2019, in 34 pages.

(56) References Cited

OTHER PUBLICATIONS

Exhibit G, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 24 pages.

Exhibit H, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 27 pages.

Exhibit I, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 34 pages.

Exhibit J, Fisher & Paykel Healthcare Limited's Disclosure of Asserted Claims and Infringement Contentions, *Fisher & Paykel Healthcare Limited* v. *Flexicare Incorporated*, Case No. 8:19-CV-00835JVS(DFMx), Aug. 19, 2019, in 29 pages.

Flexicare Incorporated's Patent L.R. 3-3 Invalidity Contentions, *Fisher & Paykel Healthcare Limited* v. *Flexicare Incorporated*, Case No. 8:19-CV-00835JVS(DFMx), Oct. 17, 2019, in 54 pages.

One page off the Perma Pure Inc. website of the product brochure #104 of the New PD TM-Series Gas Dryers.

Three pages off the SympaTex website of some of the most common questions that are asked and some technical data on the SympaTex membrane.

International Preliminary Report on Patentability in PCT/NZ2017/050074 dated Dec. 11, 2018 in 13 pages.

May 3, 2019 Complaint for Patent Infringement Demand for Jury Trial, *Fisher & Paykel Healthcare Limited* v. *Flexicare Incorporated*, Case No. 8:19-CV-00835.

European Examination Report for European Patent Application 17202695.7 dated Oct. 4, 2019.

Painter, Chris J., "Waterproof, Breathable Fabric Laminates: A Perspective from Film to Market Place", Journal of Coated Fabrics, vol. 26, Oct. 1996, pp. 107-130.

International Search Report; PCT/NZ2017/050074; dated Oct. 24, 2017.

* cited by examiner

BREATHING CIRCUIT COMPONENTS FOR RESPIRATORY APPARATUS

CROSS-REFERENCE TO RELATED APPLICATIONS

This application is a U.S. National Phase of PCT International Application No. PCT/NZ2017/050074, filed Jun. 7, 2017 and published as WO 2017/213523 on Dec. 14, 2017, which claims priority to U.S. Patent Application No. 62/346,840 filed Jun. 7, 2016. The entire disclosure of each of the above-identified application is hereby incorporated by reference.

FIELD OF THE INVENTION

The present invention relates to breathing circuit components for respiratory apparatus and in particular to components such as breathing gas conduits. Such breathing gas conduits may comprise inspiratory or expiratory gas conduits, or parts of such conduits, connected between a gas flow controller and a patient interface. Such breathing circuit components could comprise other parts of the breathing circuit, such as conduit connectors, conduit adaptors, catheter mounts, or shorter sections of breathing gas conduit for connection between a patient interface and an inspiratory gas conduit for delivering inspiratory gases to the patient interface, for example. The present invention stems from work relating to breathing gas conduits of the type described in our earlier patent applications US2001054422 and US20090126817, the entire contents of each of which are hereby incorporated herein by reference.

BACKGROUND

In respiratory apparatus, gases having high levels of relative humidity are supplied and returned through breathing gas conduits of a relatively restricted size. Buildup of condensation on the inside wall of the breathing gas conduit is a frequent result of this high humidity. In the prior art, attempts have been made to reduce the adverse effect of this condensation by either reducing the level of condensation or providing collection points in the breathing gas conduit for draining condensed liquid from the breathing gas conduit. Reducing the condensation has generally been achieved by maintaining or elevating the temperature of the gases flow and/or of the conduit wall to reduce the formation of condensation.

Our earlier application US2001054422 describes a breathing circuit component comprising an inlet, an outlet and an enclosing wall which defines a gases passageway between the inlet and the outlet. At least a region of the wall is formed from a breathable material that allows the passage of water vapour from the gases passageway, without substantially allowing the passage of liquid water or respiratory gases. Such a breathing circuit component may comprise an inspiratory or expiratory portion of the breathing circuit.

Breathing gas conduits are used in respiratory systems to convey respiratory gases between a respiratory component, such as a ventilator, high flow therapy device, or CPAP, and a patient. Respiratory gases can be heated and/or humidified prior to delivery to the patient to mimic the transformation of air that occurs as it enters the respiratory system. Breathing gas conduits in the form of inspiratory gas conduits can deliver the heated and/or humidified respiratory gases directly to a patient interface or, in some cases, an additional, usually shorter, breathing gas conduit can be located between the inspiratory gas conduit and the patient interface. The additional breathing gas conduit can be insulated and/or heated to reduce condensate formation within the breathing gas conduit. Breathable breathing gas conduits can also avoid condensate forming within the breathing gas conduit. As used herein, the term "breathable" generally means permeable or highly permeable to water vapor and substantially impermeable to liquid water and the bulk flow of gases. As used herein, the term "breathable" generally means highly permeable to water vapor and substantially impermeable to liquid water and the bulk flow of gases. A "breathable material" as used herein generally refers to a material that is highly permeable to water vapor and substantially impermeable to liquid water and the bulk flow of gases. In certain embodiments, a breathable material may have a moisture (water) vapour permeability of greater than or equal to 500 g/m$^2$/24h (or thereabout) when measured according to Procedure ASTM E 96-66 B, modified: $T_{water}$=30° C.; $T_{air}$=21° C., relative humidity=60%, air flow=2 m/s (using the upright cup method). The permeability may be greater than 750 g/m$^2$/24h, greater than 1000 g/m$^2$/24h, greater than 1500 g/m$^2$/24h, greater than 2000 g/m$^2$/24h, up to 3000 g/m$^2$/24h, or greater than or equal to about 1900 g/m$^2$/24h. Accordingly, in certain embodiments, a breathable material may have a gas impermeability of less than 200 ml*mm/m^2/day/atm. Wherein the gas may be air and the term "air" is understood to mean breathable gas of primarily oxygen and nitrogen combined, particularly excluding water vapour. A breathing circuit component and/or circuit suitable for use in the present specification may conform to standards ASTM E 96-66 B, ISO 811, and/or EN ISO 9237.

There is a desire to provide a breathing circuit component which is as easy, unobtrusive, comfortable and reliable to use as possible. It can be difficult with components of respiratory apparatus to achieve acceptance and satisfaction by the patient using such components. It has been shown that if the patient accepts and is satisfied by the respiratory apparatus, they will be more likely to continue to use the respiratory apparatus and therefore reliably receive the treatment required.

A breathing circuit component including such a breathable material may have reduced durability and may be susceptible to damage by end users.

Prior art breathing gas conduits can also be susceptible to unwanted noise during use, particularly as the breathing gas conduit is moved, flexed or bent. Such movement can cause a 'crinkling' type noise, which is undesirable. This is particularly relevant where a breathing gas conduit is being used on a spontaneously breathing patient, who may be relatively mobile.

SUMMARY

It is an object of the present invention to provide a breathing circuit component which will at least go some way towards improving on the above or which will at least provide the public and/or the medical profession with a useful choice.

An alternative object of at least one aspect of the invention is to provide a breathable breathing gas conduit which has increased durability, and/or produces less 'crinkle' noise in use.

According to a first aspect of the invention there is provided a breathing circuit component comprising:
an inlet;
an outlet;

and an enclosing wall defining a gases passageway between said inlet and said outlet, at least a region of said wall comprising a membrane that allows the passage of water vapour without substantially allowing the passage of liquid water or respiratory gases, wherein
said membrane has a thickness of about 35 to 45 micrometers.

In some embodiments, the membrane has a thickness of about 37 to 43 micrometers, or about 39 to 40 micrometers, or about 40 micrometers.

The membrane may comprise a hydrophilic polyester material. In one example, the membrane is of a material sold under the brand name Sympatex.

The breathing circuit component may be a breathing gas conduit, such as an inspiratory or expiratory gas conduit, or a short section of such a breathing gas conduit. The breathing circuit component may comprise a conduit connector, or a conduit adaptor, or a catheter mount for example.

In the example of a breathing gas conduit, the breathing gas conduit may include at least one helically wound polymer tape or strip, part or all of said strip comprising the membrane, respective edges of adjacent turns of said strip being adjoining or overlapping and bonded to form the enclosing wall. Lateral reinforcement against crushing may be provided and may comprise a helical bead disposed over said adjoining or overlapping edges between adjacent turns of the tape or strip. The pitch of the helical bead may fall within the ranges of approximately 3.5 mm to 5.5 mm, approximately 4.1 mm to 4.8 mm, and approximately 3.8 mm to 5.2 mm. In one embodiment, the pitch of the helical bead may be about 4.5 mm. The width of the bead may be between 1 and 3 mm, and in one example is about 2 mm. The height of the bead may be between 0.5 and 2 mm, and in one example is about 1 mm. The bead may comprise a thermoplastic material, and is made of a polyester based polymer material. The wall of the conduit and the bead may both comprise polyester based polymers, which improves the bond between the conduit wall and the bead. The bead may be made of a material sold under the trade name Arnitel® EM550. The polymer used for the bead may be mixed with a pigment.

In another example, the lateral reinforcement may comprise a series of annular ring beads or ribs distributed over the length of said breathing gas conduit.

The breathing gas conduit may have a ratio of bead pitch to membrane wall thickness in the range of 1:0.0080 to 1:0.0128, in the range of 1:0.0080 to 1:0.0118, and in one embodiment of 1:0.0088. According to these ratios and the non-limiting values provided hereinabove for the bead pitch, the membrane wall thickness may be between 35 to 45 micrometers, 37 to 43 micrometers, 39 to 40 micrometers, or 40 micrometers.

In some examples the length of the gases passageway between the inlet and the outlet may be in the range of approximately 310 mm to 410 mm. The length of the gases passageway between the inlet and the outlet may be about 370 mm, and generally within a range of 360 mm to 380 mm.

The inner diameter of the breathing gas conduit may be in the range of 10 to 15 mm, or 11.4 mm to 12.2 mm and in one example is 11.8 mm.

The breathing gas conduit may include longitudinal reinforcement against stretching of the breathing gas conduit.

The breathing gas conduit may include a heater wire extending along, through, or wound around, the gases passageway of the breathing gas conduit. The heater wire may be embedded in the helical bead or ribs for example. More than one heater wire may be provided.

The breathing gas conduit may include a sensor wire extending along, through, or wound around, the gases passageway of the breathing gas conduit. The sensor wire may be embedded in the helical bead or ribs for example. More than one sensor wire may be provided. The breathing gas conduit may further comprise one or more sensors in communication with the one or more sensor wire.

The breathing circuit component may have a wall entirely formed by the membrane.

The breathing circuit component may be resistant to extension forces up to approximately 30 Newton and/or at least of 15 to 30 Newton in the longitudinal direction, that is in the direction of the longitudinal axis of the gases passageway, without permanent deformation. In another embodiment of the present invention, the breathing circuit is resistant to extension forces up to approximately 25 Newton in the longitudinal direction.

The breathing may be resistant to an applied force up to approximately 15 Newton and/or at least of 10 to 15 Newton in the lateral direction, that is in a direction transverse to the longitudinal axis of the gases passageway, without the breathing circuit component breaking. In a further embodiment of the present invention, the breathing circuit component is resistant to an applied force of approximately 13 Newton in the lateral direction.

In a further aspect of the present invention, the breathing circuit component may comprise an inlet, an outlet; and an enclosing wall defining a gases passageway between the inlet and the outlet, at least a region of the wall comprising a membrane that allows the passage of water vapour without substantially allowing the passage of liquid water or respiratory gases; wherein, the breathing circuit component is resistant to extension forces up to approximately 30 Newton in the longitudinal direction; that is in the direction of the longitudinal axis of the gases passageway, without permanent deformation.

The breathing circuit component may be resistant to extension forces of at least 15 to 30 Newton in the longitudinal direction, that is in the direction of the longitudinal axis of the gases passageway, without permanent deformation. In another embodiment of the present invention, the breathing circuit component o is resistant to extension forces up to approximately 25 Newton in the longitudinal direction.

In another aspect of the present invention, a breathing circuit component may comprise an inlet, an outlet, and an enclosing wall defining a gases passageway between the inlet and the outlet, at least a region of the wall comprising a membrane that allows the passage of water vapour without substantially allowing the passage of liquid water or respiratory gases, wherein, the breathing circuit component is resistant to an applied force up to approximately 15N in the lateral direction, that is in a direction transverse to the longitudinal axis of the gases passageway, without the breathing circuit component breaking.

The breathing circuit component may be resistant to an applied force of between 10 to 15 Newton in the lateral direction, that is in a direction transverse to the longitudinal axis of the gases passageway, without the breathing circuit component breaking. In a further embodiment of the present invention, the breathing circuit component is resistant to an applied force of approximately 13 Newton in the lateral direction.

The breathing circuit may further comprises a reinforcing element such as a bead or rib, which supports and reinforces the enclosing wall, wherein the breathing circuit component is resistant to an applied force up to approximately 15 Newton in the lateral direction, that is in a direction transverse to the longitudinal axis of the gases passageway, without the breathing circuit component delaminating such that the reinforcing element separates from the enclosing wall.

The enclosing wall of the breathing circuit component may define a gases passageway is entirely comprised of a breathable membrane.

In a further aspect of the present invention, a breathing gas conduit for a respiratory apparatus is provided and comprises: an inlet; an outlet; and an enclosing wall defining a gases passageway between the inlet and the outlet, at least a region of the wall comprising a membrane that allows the passage of water vapour without substantially allowing the passage of liquid water or respiratory gases; wherein, the membrane has a thickness of about 35 to 45 micrometers.

The membrane may have a thickness of about 37 to 43 micrometers, 39 to 40 micrometers, or be of 40 micrometers.

In an aspect of the present invention, a breathing gas conduit for a respiratory apparatus is provided and comprises: an inlet; an outlet; an enclosing wall defining a gases passageway between the inlet and the outlet, at least a region of the wall comprising a membrane that allows the passage of water vapour without substantially allowing the passage of liquid water or respiratory gases, the membrane having a membrane wall thickness; and a bead or rib helically wound around the enclosing wall, the bead having a bead pitch being the distance between adjacent winds of the bead; wherein, the breathing gas conduit has a ratio of bead pitch to membrane wall thickness in the range of 1:0.0080 to 1:0.0128.

The ratio of bead pitch to membrane thickness may be in the range of 1:0.0080 to 1:0.0118 and/or 1:0.0088.

In another aspect of the invention, a breathing gas conduit kit for a respiratory apparatus is provided and comprises: a breathing gas conduit having an inlet, an outlet, and an enclosing wall defining a gases passageway between the inlet and the outlet; a conduit connector configured to be connected to the inlet or the outlet; and the breathing circuit component of the different embodiments described hereinabove, wherein the breathing circuit component is configured to be connected to the breathing gas conduit with the conduit connector.

The breathing gas conduit kit may further comprise a patient interface being any one of:
a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose; and
f) a hybrid mask comprising a combination of nasal pillows/prongs and an oral seal.
g) an endotracheal conduit; and
h) a tracheostomy interface.

The breathing gas conduit kit may further comprise a humidification chamber configured to humidify breathing gas.

In a further aspect of the present invention, a respiratory apparatus for delivering a flow of breathable gas to a patient is provided and comprise: a humidifier configured to humidify a flow of breathable gas received from a gas source; and a breathing circuit component configured to be in fluid communication with the humidifier.

The respiratory apparatus may further comprise a blower configured to generate the flow of breathable gas.

The respiratory may further comprise an inspiratory gas conduit configured to be connected between the humidifier and the breathing circuit component. The inspiratory gas conduit may also comprise a heater element configure to heat gases flowing through the inspiratory gas conduit.

The respiratory apparatus may further comprise a patient interface configured to be in fluid communication with the breathing circuit component to deliver breathable gas to or from the patient. The patient interface may be any one of:
a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose; and
f) a hybrid mask comprising a combination of nasal pillows/prongs and an oral seal.
g) an endotracheal conduit; and
h) a tracheostomy interface.

In another aspect of the present invention, a breathing circuit component kit is provided and comprises:
a) any of the presently disclosed breathing circuit component; and
b) a patient interface.

The patient interface may be any one of:
a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose;
f) a hybrid mask comprising a combination of nasal pillows/prongs and an oral seal;
g) an endotracheal conduit; and
h) a tracheostomy interface.

The breathing circuit component kit may further comprise any one or more of:
a) a lanyard configured to be attached at or adjacent a first end of the breathing circuit component;
b) a conduit connector configured to connect a first end of the breathing circuit component to an inspiratory gas conduit;
c) an inspiratory gas conduit configured to deliver inspiratory gases to the patient interface via the breathing circuit component;
d) a humidifier configured to humidify inspiratory gases prior to delivery of the gases to the patient interface; and/or
e) a gases source configured to supply a flow of inspiratory gases to the patient interface via the breathing circuit component.

The inspiratory conduit may comprise a heating element configured to heat the gases as the gases flow along the inspiratory conduit.

At least the humidifier and the gas source may be integrated such that the humidifier and the gas source are contained in a single housing.

Hereinafter, throughout the description and claims, it is to be understood that a material that allows the passage of water vapour without substantially allowing the passage of liquid water or respiratory gases may be described as a "breathable" material. Materials may be breathable due to their composition, physical structure, or a combination thereof. As used herein, the term "breathable" generally means highly permeable to water vapor and substantially impermeable to liquid water and the bulk flow of gases. A "breathable material" as used herein generally refers to a material that is highly permeable to water vapor and substantially impermeable to liquid water and the bulk flow of gases. In certain embodiments, a breathable material may have a moisture (water) vapour permeability of greater than or equal to 500 g/m$^2$/24h (or thereabout) when measured according to Procedure ASTM E 96-66 B, modified: $T_{water}$=30° C.; $T_{air}$=21° C., relative humidity=60%, air flow=2 m/s (using the upright cup method). The permeability may be greater than 750 g/m$^2$/24h, greater than 1000 g/m$^2$/24h, greater than 1500 g/m$^2$/24h, greater than 2000 g/m$^2$/24h, up to 3000 g/m$^2$/24h, or greater than or equal to about 1900 g/m$^2$/24h. Accordingly, in certain embodiments, a breathable material may have a gas impermeability of less than 200 ml*mm/m^2/day/atm. Wherein the gas may be air and the term "air" is understood to mean breathable gas of primarily oxygen and nitrogen combined, particularly excluding water vapour. Typically, a breathing circuit component and/or circuit suitable for use in the present specification may conform to standards ASTM E 96-66 B, ISO 811, and/or EN ISO 9237.

For example, the length of the gases passageway between the inlet and the outlet may be in the range of approximately 310 mm to 410 mm, or 360 mm to 380 mm, and in one example is 370 mm.

Those skilled in the art will appreciate that a respiratory system as herein described can refer to any system suitable for delivering respiratory gases to a patient, such as, for example but not limited to, oxygen, carbon dioxide, air and/or any combination of suitable respiratory gases to a patient. Similarly, it will be appreciated that the patient may be receiving any type of therapies such as, for example but not limited to, high flow therapy (HFT), such as nasal high flow therapy (NHFT), treatment for obstructive sleep apnea (OSA), invasive ventilation (INV), or non-invasive ventilation (NIV).

Such a respiratory system may include one or more respiratory components which can refer to, but is not limited to, a gases source, flow generator, humidification apparatus, humidification chamber, or medical conduit.

A breathing gas conduit as herein described can refer to a gas conduit, such as for example but not limited to, an inspiratory gas conduit, expiratory gas conduit, or interface gas conduit that connects between a respiratory component and a patient interface.

A gas source as herein described can refer to an apparatus that supplies gas or gases to a respiratory system such that the gas or gases can be delivered to a patient. The gas source can, for example but not limited to, take the form of ambient air, a wall source, or a gas canister. It will be further appreciated by those skilled in the art that a flow generator as herein described can refer to any apparatus suitable for delivering a flow of gas to a respiratory system such as, for example but not limited to, a ventilator, a blower, an air compressor, etc. In some cases, the flow generator may be integrated with a humidification apparatus. In some cases the gas source may be remote from the respiratory system, with the respiratory system comprising a suitable gas inlet port configured for connection to the remote gas source.

Further aspects of the invention, which should be considered in all its novel aspects, will become apparent from the following description.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

DESCRIPTION OF THE DRAWINGS

One preferred form of the invention will now be described with reference to the accompanying drawings in which.

DETAILED DESCRIPTION

Figure 1:
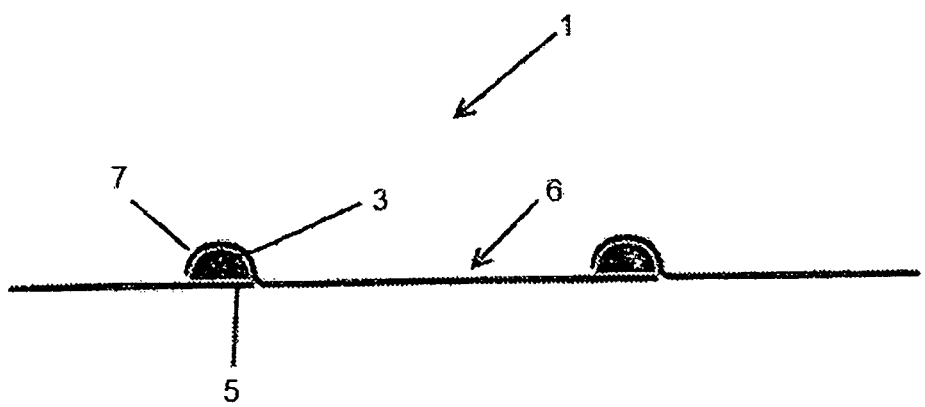
FIG. 1 is a schematic cross-sectional view of a single walled breathing gas conduit formed by applying a reinforcing bead to overlapping spirally wound thin film layers forming the wall of the conduit, constructed and operative in accordance with an embodiment of the present invention.

In accordance with the invention there is provided a breathing circuit component at least part of which comprises a breathable material. The breathing circuit component may comprise a breathing gas conduit such as an entire inspiratory or expiratory gas conduit, or a short length or part of a conduit. By 'short', we mean shorter than the inspiratory or expiratory gas conduit. For example, the length of the gases passageway between the inlet and the outlet may be in the range of approximately 310 mm to 410 mm, or approximately 360 mm to 380 mm and is in one embodiment 370 mm.

In an embodiment, the breathing circuit component may comprise a short section of breathing gas conduit, one end of which is configured to be connected to a patient interface. The breathing circuit component may comprise a mask adaptor configured to be connected between a patient interface and a breathing gas conduit. The other end of the short section of breathing gas conduit may comprise or be provided with a conduit connector for connecting to a gas conduit. The breathing circuit component may therefore be packaged and sold as an assembly or kit comprising a conduit connector, the short section of breathable gas conduit and a patient interface (optionally also including a lanyard and/or mask connector). The patient interface may comprise any of:

a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose;
f) a hybrid mask comprising a combination of nasal pillows/prongs and an oral seal;
g) an endotracheal conduit; and
h) a tracheostomy interface.

In alternative embodiments, the breathing circuit component may comprise a conduit connector or adaptor to which a breathing gas conduit such as an inspiratory or expiratory gas conduit may be connected.

The breathing circuit component may primarily comprise an inlet, an outlet, and an enclosing wall defining a gases passageway between said inlet and said outlet. At least a region of said wall comprises a membrane that is of a breathable material. Substantially the entire length of the breathing circuit component may be configured to allow the passage of water vapour without substantially allowing the passage of liquid water or respiratory gases.

As used herein, the term "breathable" generally means highly permeable to water vapor and substantially impermeable to liquid water and the bulk flow of gases. A "breathable material" as used herein generally refers to a material that is highly permeable to water vapor and substantially impermeable to liquid water and the bulk flow of gases. In certain embodiments, a breathable material may have a moisture (water) vapour permeability of greater than or equal to 500 g/m$^2$/24h (or thereabout) when measured according to Procedure ASTM E 96-66 B, modified: $T_{water}$=30° C.; $T_{air}$=21° ° C., relative humidity=60%, air flow=2 m/s (using the upright cup method). The permeability may be greater than 750 g/m$^2$/24h, greater than 1000 g/m$^2$/24h, greater than 1500 g/m$^2$/24h, greater than 2000 g/m$^2$/24h, up to 3000 g/m$^2$/24h, or greater than or equal to about 1900 g/m$^2$/24h. Accordingly, in certain embodiments, a breathable material may have a gas impermeability of less than 200 ml*mm/m^2/day/atm. Wherein the gas may be air and the term "air" is understood to mean breathable gas of primarily oxygen and nitrogen combined, particularly excluding water vapour. Typically, a breathing circuit component and/or circuit suitable for use in the present specification may conform to standards ASTM E 96-66 B, ISO 811, and/or EN ISO 9237.

The membrane may have a thickness of about 35-45 micrometers. In one embodiment, the breathing circuit component is resistant to extension forces in the longitudinal direction, that is, in the direction of the longitudinal axis of the gases passageway, without permanent deformation, up to 30 N, and at least in the range of 20 to 30N. In one embodiment of the present invention, the breathing circuit component is resistant to extension forces in the longitudinal direction of about 25N. In one embodiment the breathing circuit component is resistant to a longitudinal pull force up to 55 N, and at least between 45 and 55 N, before breaking in the direction of the longitudinal axis of the component. In one embodiment of the present invention, the breathing circuit component is resistant to a longitudinal pull force of between 49 N to 54 N, and in one embodiment about 52 N. In one embodiment, the breathing circuit component is resistant to applied forces in the lateral direction that is, in a direction transverse to the longitudinal axis of the gases passageway, without breaking (such as, for example, by puncturing or delaminating), in the range of 11.5 N to 13.5 N, in one embodiment 12 N to 13 N, and in one embodiment about 12.5N.

In the example of the breathing circuit component comprising a membrane reinforced and/or supported by a helical bead or rib, delamination testing was conducted by applying a force to the membrane in a lateral direction until the membrane broke or 'delaminated' from the bead. The applied force was applied in the lateral direction by forcing a probe into the membrane by a pre-set distance. During the test, the peak force was displayed by a force gauge forming part of the testing apparatus. The test passes if the resulting force exceeds a predetermined set value indicating that yield in the breathable film has occurred before any delamination.

The breathing gas conduit may include at least one helically wound polymer tape or strip, part or all of said strip comprising the membrane, respective edges of adjacent turns of said strip being adjoining or overlapping and bonded to form the enclosing wall. The breathing gas conduit may include lateral reinforcement against deformation of the breathing gas conduit, such as a helical bead disposed over said adjoining or overlapping edges between adjacent turns of strip, or a series of annular ring beads or ribs distributed over the length of said conduit. The bead may be formed from a thermoplastic material such as, for example but not limited to, a polyester based polymer. The tape or strip and bead may both be made from a polyester based polymer, which improves the bond between them. The bead may be made of a material sold under the trade name Arnitel® EM550.

The breathing gas conduit may further or alternatively include longitudinal reinforcement against stretching of the breathing gas conduit.

Figure 18A:
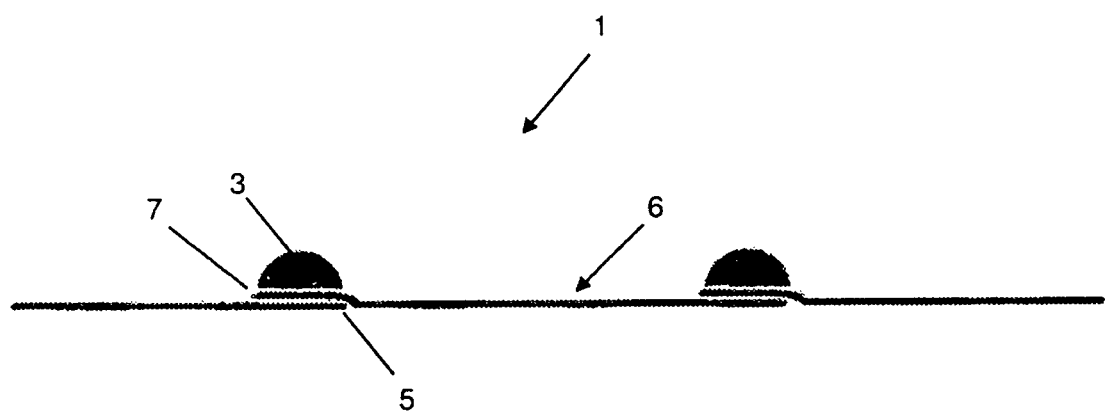
FIGS. 18A and 18B are schematic cross-sectional views of different configurations for the single walled breathing gas conduit and the helical bead, constructed and operative in accordance with further embodiments of the present invention.

Referring to FIG. 1, a breathing circuit component comprising a breathing gas conduit 1 is shown according to an example method of manufacture of a single walled breathing gas conduit. This method may be particularly suited to thin walled conduits. The thin film 6 is arranged in a spiral or helix such that the edge portions of adjacent layers overlap and form the wall of a breathing gas conduit 1. Interposed the overlapping edges of adjacent winds of film 6 is a reinforcing element comprising a bead 3 of polymer material bonded with the overlapping portions of film 6 sealing the joint between windings and forming a continuous breathing gas conduit 1. The seam is formed between the edge 5 of a first layer of film 6 and the edge 7 of a second, adjacent layer of film 6 which is laid over top of the polymer bead 3 while the bead is molten. The overlapping layer of film, because it is so thin, follows the contour of the bead 3 very closely and results in a smooth inner conduit wall. In another embodiment of the present invention illustrated on FIG. 18A, the bead 3 is not interposed between overlapping edges of adjacent winds of film 6 but rather is disposed on both layers. More specifically, the thin film 6 is arranged first in a spiral or helix such that edge portions of adjacent layers overlap. Then, the bead 3 of polymer material is disposed on the overlapping edges of the thin film 6 so as to form the breathing gas circuit.

Figure 18B:
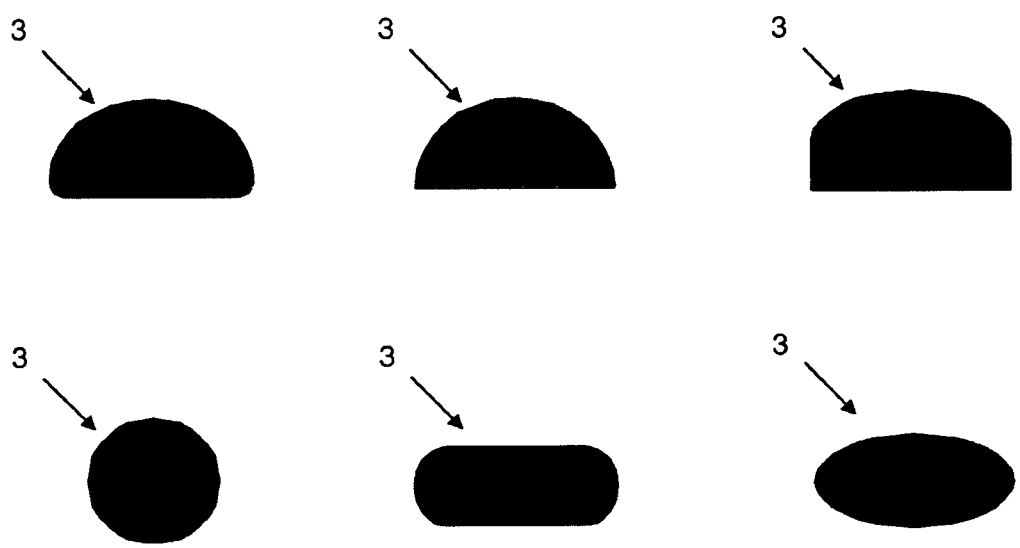

As it is apparent from FIG. 1, the bead 3 has a softened 'D' shape or half-circle shape, with the flat side of the 'D' located on the inside. This particular shape ensures that the interior surface of the wall of the breathing gas conduit 1 is substantially flat, thereby minimizing the resistance to flow. The bead 3 may be extruded as a circle (i.e. the die of the extrusion device may have a circular cross section) and interposed between/disposed on the overlapping edges of the thin film 6. The bead 3 typically acquires its 'D' or half-circle shape when it is spirally drawn into/onto the thin film 6 structure and after cooling. Those skilled in the art will appreciate that the shape of bead 3 is not limited to this particular shape but rather that any suitable profile shapes such as, for example but not limited to, circle, oval, 'pill', and variations of the D-shape, may be used. FIG. 18B illustrates these different shapes/variations for the bead.

Those skilled in the art will further appreciate that although the breathing gas circuit 1 of FIG. 1 is formed as a single spiral or helix, any other suitable configurations may be possible. For example, but not limited to, the breathing gas circuit 1 may be formed as a double spiral structure of thin film 6 and comprise two beads. Additionally and/or alternatively, the breathing gas circuit 1 may comprise one or more heater or sensor wires. These wires may be disposed within the gases passageway formed by the wall of the breathing gas circuit 1 and/or outside the gases passageway. In another embodiment, one or more wires may be incorporated in the bead. In a further embodiment in which the breathing gas circuit is formed as a double spiral structure, each bead may include a single wire.

It will be further appreciated that in all the different variations and/or configurations provided hereinabove and later in this specification, the helical bead is provided as a reinforcement/reinforcing element not being part of the wall and/or membrane.

In the example of the breathing circuit component being a breathing gas conduit, such a conduit may take a number of forms but typically comprises a breathable membrane which defines a water vapour flow passageway. Water vapour is allowed to diffuse out through the membrane wall before it has an opportunity to condense into liquid water within the breathing gas conduit. Build-up of condensation inside the breathing gas conduit is therefore avoided, which eliminates the need for a condensation collector in the breathing gas conduit or clinician intervention to drain the breathing gas conduit of condensation. Where the breathing gas conduit is connected to a patient interface, avoiding the build-up of condensation inside the breathing gas conduit also avoids or at least reduces the formation of condensation in the patient interface or on the patient's skin.

The breathable, or part breathable membrane which allows passage of water vapour may comprise all or part the breathing circuit component. Thus water vapour can diffuse only from selected parts of the gas flow passageway defined through the breathing circuit component.

The membrane may be supported or partially supported and/or reinforced by one or more ribs or beads helically wound about the interior or the exterior of the membrane. The bead may be of a metal or polymer material, or a combination of both. The bead may comprise one or more electrically conducting elements for heating the conduit and/or connection to one or more sensors. Sensors for determining properties of the gases, such as temperature, flow rate, humidity, gases concentration or pressure, may be embedded in the bead or membrane of the breathing gas conduit, or may be provided at, or connected to, one or both ends of the breathing gas conduit.

Figure 2:
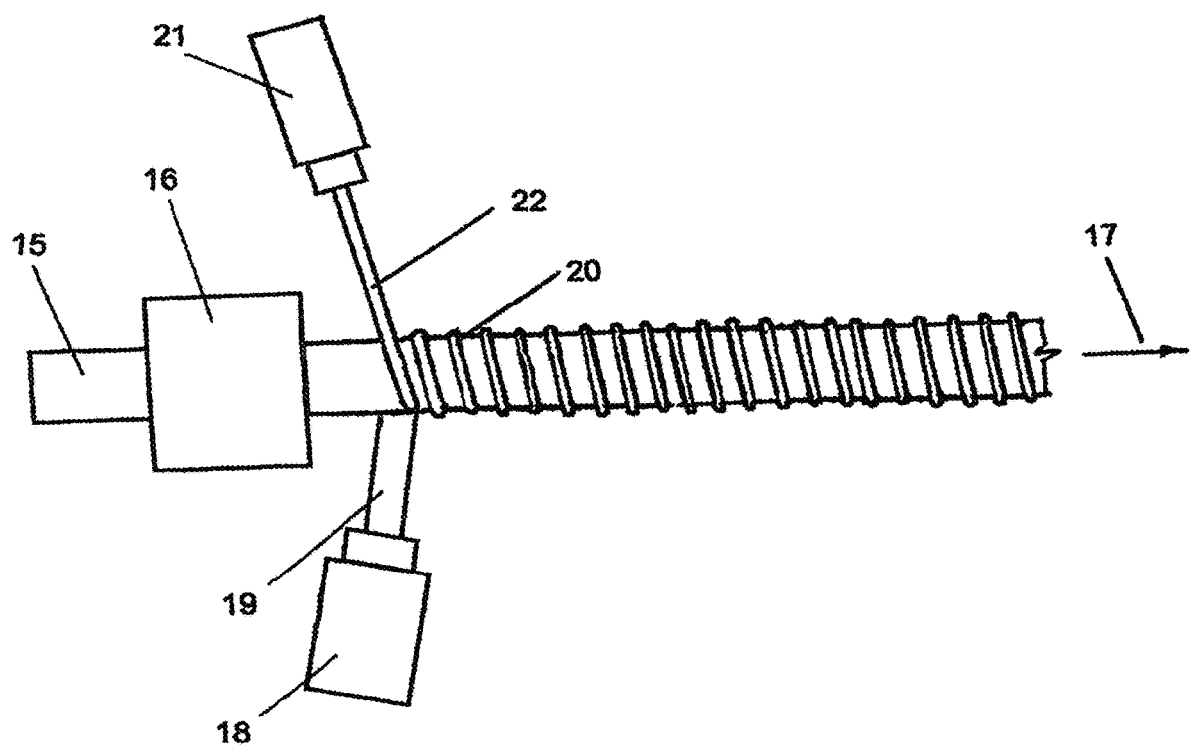
FIG. 2 is a plan view of a breathing gas conduit forming device for forming the breathing gas conduit of FIG. 1.

An example of forming apparatus suitable for manufacturing a breathing circuit component, such as a breathing gas conduit according to an embodiment of the present invention described above, is shown in FIG. 2.

The apparatus includes a former 15 having a plurality of rotating rods arranged around a central support rod. The rods extend from and are rotated by a gearbox within a machine stock 16. At least in the conduit forming region the rotating rods follow a helical path. The pitch angle of the rods relative to the support rod controls the pitch angle of the breathing gas conduit being formed.

The breathing gas conduit being formed on the former is rotated and advanced in the direction of arrow 17 by the movement of the rotating rods. The advance speed of the former is selected relative to the rotational speed so that the pitch of the helical laying of the strip or tape on to the former 15 is a little less than the width of the strip so that adjacent turns narrowly overlap. A first extruder 18 extrudes a tape 19 of thin film polymer materials. The tape 19 deposits on the former 15 in a helical fashion by action of the former. The pitch of the helical disposition of tape 19 is slightly less than the width of tape 19. The helical deposition of tape 19 forms the wall 20 of the breathing gas conduit. A second extruder 21 extrudes a bead 22 of polymer material. The molten bead 22 deposits between the overlapping portions of adjacent winds of tape 19 and is sufficiently heated to weld to the strips of tape 19. Applying the molten bead between the overlapping layers of tape may improve the weld quality as both layers of tape that are to be welded are in physical contact with the molten bead. The quality of the surface finish for the inner surface of a breathing gas conduit is important, as a rough inner surface may hinder gases flow and contribute to more condensation to building up in the conduit. The above described construction technique is especially suited to conduits fabricated from thin film. The thin film is able to conform to the shape of the raised rib of the applied molten bead 22 during fabrication. By lapping very closely onto the bead and wrapping around the bead) the thin film maintains a smooth inner surface on the finished conduit product as shown in FIG. 1. It is desirable for the ribbon to be sufficiently supple at least laterally, to conform along its overlapping portion to the contour of the bead, so that the overlapping ribbon may meet or substantially meet the underlapping ribbon at the edge of the bead.

In addition to the bonding of the film to the molten bead between adjacent overlapping layers, other active fusing techniques may be applied. Active methods may include, for example, hot air welding, hot rollers or radio frequency welding.

It will be appreciated that the above described breathing gas conduit and methods of manufacture are provided as examples of the type of thin walled conduits to which the present invention may be applied. The examples have been chosen to illustrate the many possible variations and are not meant to be in any way limiting. Many further variations will present themselves to those skilled in the art. While some embodiments of the present invention have been described and convey particular advantages over other embodiments other combinations may prove commercially useful.

Figure 5:
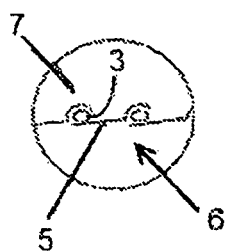
FIG. 5 is a schematic cross-sectional view of the wall of the breathing gas conduit of FIGS. 3 and 4.
Figure 13:
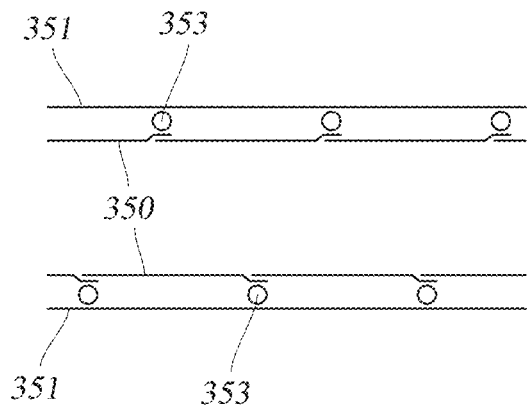
FIG. 13 is a schematic cross sectional view of a limb for a breathing circuit according to a still further variant of the present invention.

The accompanying FIGS. 1, 5 and 13 show small gaps or spaces between the reinforcing bead and the overlapping portion of ribbon or tape. It is to be understood that these spaces are present for illustration purposes only, in order to differentiate the bead from the overlapping layer in the diagrams. In practice the overlapping layer conforms to the bead and bonds, without forming large gaps or bubbles.

Figure 3:
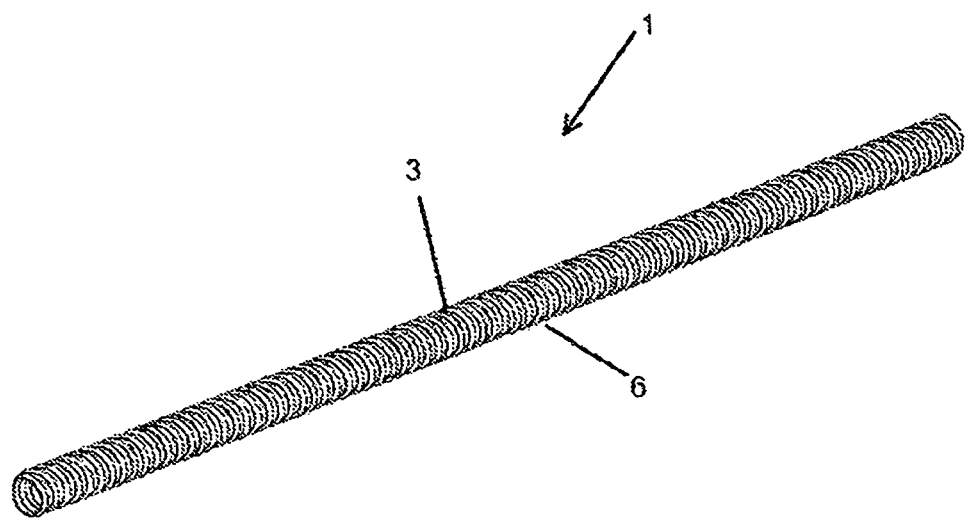
FIG. 3 is a perspective view of a breathing gas conduit, constructed and operative in accordance with an embodiment of the present invention.
Figure 4:
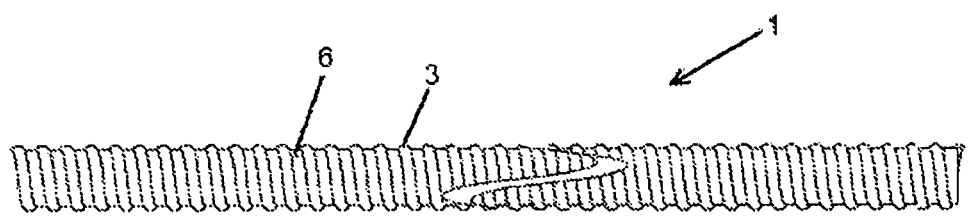
FIG. 4 is a side view of the breathing gas conduit of FIG. 3.

Referring to FIGS. 3 to 5, a breathing circuit component comprising a breathing gas conduit 1 is shown comprising a membrane defining a conduit wall 6 formed from adjacent layers of film 5, 7, each layer 5, 7 being bonded to the next via a helical bead 3.

Figure 6:
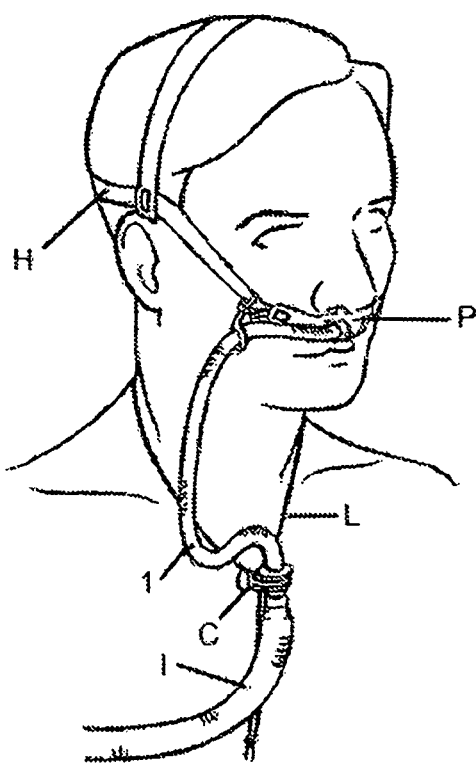
FIG. 6 is a perspective view of a short breathing gas conduit connected between an inspiratory gas conduit, and a patient interface comprising a nasal cannula, constructed and operative in accordance with an embodiment of the present invention.
Figure 7:
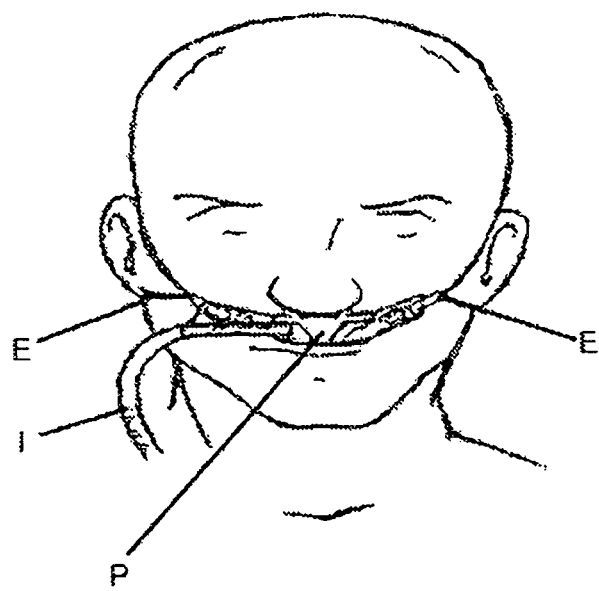
FIG. 7 is a front view of another patient interface showing the short breathing conduit of FIG. 6.
Figure 8:
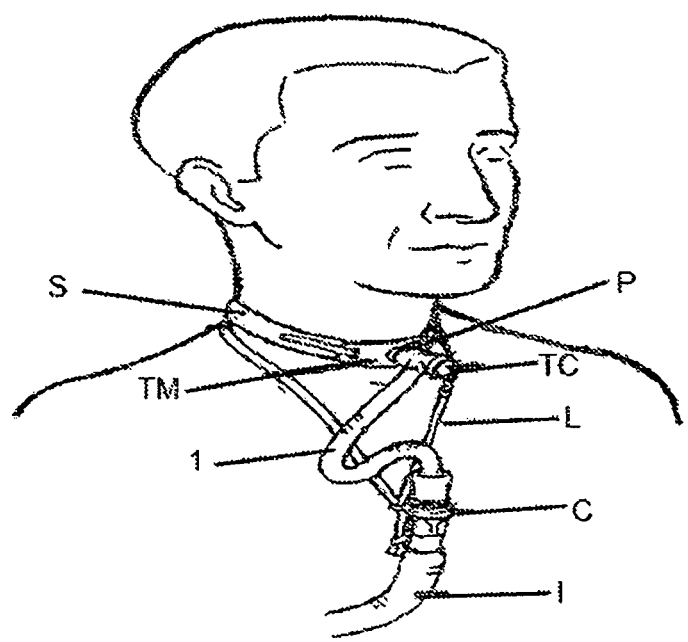
FIG. 8 is a perspective view of a short breathing gas conduit connected between an inspiratory breathing gas conduit, and a patient interface comprising a tracheostomy interface, constructed and operative in accordance with another embodiment of the present invention.

Referring to FIGS. 6 to 8, various embodiments of a breathing circuit component in accordance with the present invention are shown. In these embodiments, the breathing circuit component comprises a relatively short length of breathing gas conduit 1 connected between a patient interface P and an inspiratory gas conduit I, which may or may not be heated. The short length of breathing gas conduit 1 is shorter than the inspiratory gas conduit I.

With reference to FIG. 6, the patient interface P comprises nasal prongs held on the head of the patient by suitable headgear H. In the illustrated example the nasal prongs are non-sealing prongs which do not substantially seal against the patient's nares. With reference to FIG. 7, the same breathing gas circuit 1 is shown but used with a different patient interface P. The patient interface P comprises nasal prongs held on the head of the patient by suitable earloops E. With reference to FIG. 8, the patient interface P comprises a tracheostomy interface held on the neck of a patient by a suitable neck strap S. The upper end of the inspiratory gas conduit I, and the associated conduit connector C, are hung from the neck of the patient by a suitable lanyard L.

With reference to FIGS. 6 to 8, the short length of breathing gas conduit 1 may comprise an unheated flexible section of breathing gas conduit placed proximal to the patient to reduce torsion or pulling on the patient interface P and reduce possible heat problems or over heating close to the patient. In order to reduce condensate forming in the unheated breathing gas conduit 1, the conduit 1 is breathable, having vapour transmission properties as described above with reference to FIGS. 1 to 5.

An advantage of providing the short section of breathable breathing gas conduit 1 is that a majority of humidity in the gases is transported to the patient, and there is a relatively low loss of humidity through the breathable wall of the short breathing gas conduit 1, while condensate is reduced. This short breathing gas conduit 1 is envisaged to be used with any longer breathing gas conduit delivering heated and humidified gases to a patient.

A neck tie or lanyard L may be provided. FIG. 6 shows such a lanyard. The lanyard L may be connected to the inspiratory gas conduit I or to the connection between the inspiratory gas conduit I and the breathing circuit component. A toggle may be provided with the lanyard L in order to adjust the lanyard's length. The lanyard has the purpose of taking some of the weight of the inspiratory gas conduit I and prevents the weight of the inspiratory gas conduit I pulling on the nasal cannula assembly. This helps to prevent the prongs interfering with the sensitive lining of the nasal passages and allows the patient interface to remain in the appropriate position on the face.

The tie or lanyard L described may be used with any patient interface that supplies gases to a patient; for example it may be used with a nasal or face mask or with a tracheostomy fitting or connector. When the tie or lanyard L is used with such an interface it takes the weight of the breathing gas conduit(s) supplying gases to the mask, connector or cannula and helps reduce the pull on the mask, connector or cannula.

Referring to FIG. 7, a nasal cannula attachment device may be provided to hold the nasal cannula assembly to the patient's face. The attachment device in FIG. 7 is in the form of ear loops E that are connected to the straps of the face mount part of the nasal cannula assembly.

The loops E extend from the face mount part around the patient's ears, and provide rigid anchoring when an inelastic material is used. The loops E may be made from a thin, round cord with the ends captured in plastic, and may be adjustable. The plastic ends of the loops E are inserted into purpose made cavities in the straps, enabling adjustment of length for a comfortable, yet firm fit.

FIG. 8 shows a patient interface P comprising a tracheostomy interface that utilises a neck tie or lanyard L. The tracheostomy interface comprises a tracheostomy connector TC which attaches to a tracheostomy mount TM that extends into a tracheostomy tube (not shown) through a hole in a patient's neck and into their airway passages. The tracheostomy interface provides a direct coupling of a breathing circuit component comprising a relatively short breathing gas conduit 1 to the breathing supply of gases received through a longer inspiratory gas conduit I.

Excess weight on the tracheostomy tube may cause excess movement of the tracheostomy tube, with the risk of complications such as displacement or recannulation of the tracheostomy, the formation of granulation tissue or more seriously, stomal erosion. To obviate or reduce these problems a tie or lanyard L can be connected to the inspiratory gas conduit I or the breathing gas conduit 1, or to an additional connector (that may for example connect the breathing gas conduit 1 to the inspiratory gas conduit I). The tie or lanyard L transfers the weight of the conduits 1, I and tracheostomy connector TC from the tracheostomy tube or mount TM and distributes it onto the neck of the patient leaving a minimal load directly on the tracheostomy tube or mount TM. The tie or lanyard L may be adjustable so that the tie or lanyard L length can be altered to suit a patient's requirements.

Figure 9:
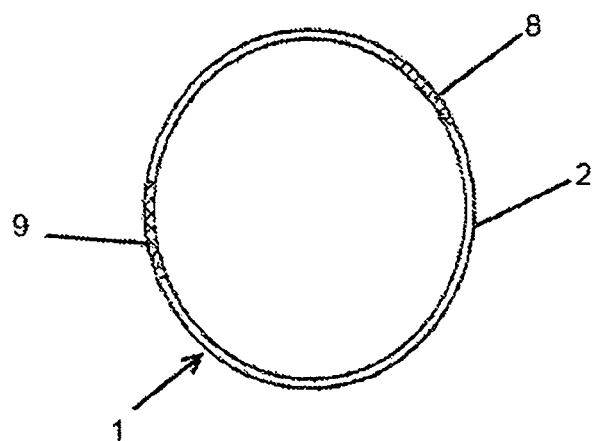
FIG. 9 is a cross-sectional view of a breathing gas conduit according to one embodiment of the present invention.

Referring to FIG. 9, in one embodiment of the invention a breathable breathing circuit component comprising a breathing gas conduit 1 is formed having one or more longitudinal strips 8, 9 of breathable membrane as part of the wall 6 thereof.

A suitable material for the breathable membrane is a hydrophilic polyester block copolymer formed into a homogeneous flat film. An example of such a film is sold under the brand SYMPATEX(R). This material is particularly suited to thin film productions.

A further variation is depicted in FIG. 13. In this figure the flexible wall membrane of the breathing gas conduit is supplemented by reinforcing to provide resistance to lateral crushing and to longitudinal stretching of the breathing gas conduit.

Figure 11:
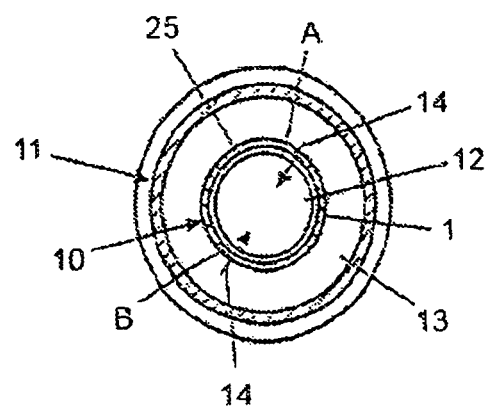
FIG. 11 is a cross sectional elevation view of a coaxial breathing circuit incorporating a breathing gas conduit, constructed and operative in accordance with a further embodiment of the present invention.
Figure 12:
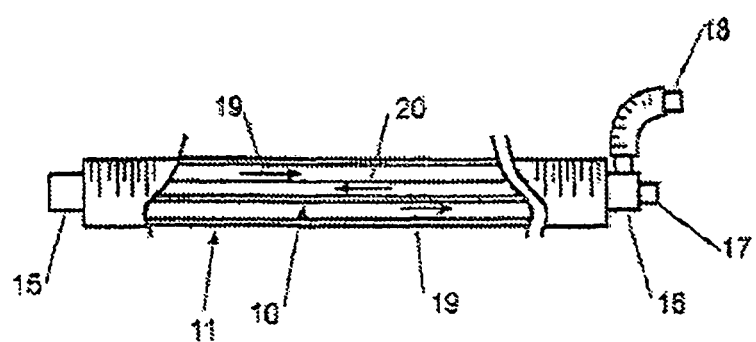
FIG. 12 is a side elevation view in partial cross section of the coaxial breathing circuit of FIG. 11.

Referring to FIGS. 11 and 12 a further aspect of the present invention is shown in which a breathing circuit component comprising a breathing gas conduit according to the present invention is provided as the inner conduit of a coaxial conduit configuration, such that expiratory gases and inspiratory gases each flow in one of the inner conduit or the space between the inner conduit and the outer conduit and in use water vapour but not liquid water is transmitted from the expiratory gases passageway to the inspiratory gases passageway. The water vapour from the expiratory gases humidifies the inspiratory gases, providing a passive gas humidification system.

In another embodiment, the breathing circuit component in accordance with the invention may comprise a catheter mount. The application of the invention to a catheter mount is described with reference to FIG. 14.

It would be possible alternatively, to have one or more longitudinal sections (lengths) of the breathing gas conduit being formed of the breathable material or isolated regions of the conduit wall being formed from the material. The embodiments described herein may be preferable due to their apparent simplicity of manufacture, being capable of linear manufacture, either by continuous stitching, gluing or welding, by co extrusion or by winding onto a former, using an example apparatus as per FIG. 2.

Figure 10:
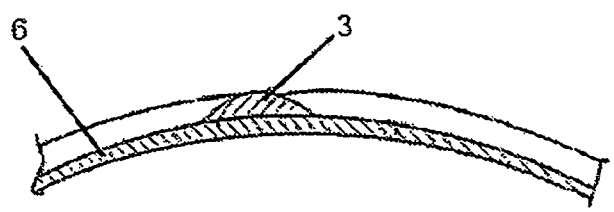
FIG. 10 is a cross sectional view of a section of a breathing gas conduit wall according to one possible construction.

Referring to FIGS. 10 and 13, a spiral, helical or longitudinal internal (or external) reinforcing members, or a series of annular hoop reinforcing members, may be provided outside (or inside) the tubular membrane to provide support. The supporting members may for example be formed from polymer plastic materials, such as the material used in the wall of the breathing gas conduit (not being the breathable regions), or alternatively may for example be a metal wire support, such as drawn steel wire, or from a combination of materials such as a polymeric material with an embedded metal element for example.

The breathing gas conduit shown in FIG. 10 may be formed in any one of a number of methods. For example the tubular membrane may be supplied in a continuous conduit. Alternatively it might be supplied in tape form. Supplied as extruded tape, the membrane may be wound helically onto a former. The helical supporting rib, provided in a semi molten state is then laid on the overlap between adjacent turns. The heat from the helical supporting rib bonds the two adjacent strips with the rib forming a flexible resilient conduit once cooled.

An embodiment of a breathing gas conduit including longitudinal reinforcement is depicted in FIG. 13. This embodiment utilizes longitudinal reinforcing threads running parallel to the axis of the conduit. Additionally and/or alternatively, mesh sheath may also be used as longitudinal reinforcement.

In the embodiment of FIG. 13 the breathing gas conduit includes an inner breathable polymer wall 350. A helical bead 353 is fused or adhered to the inner breathable wall 350. A plurality of reinforcing threads 351 running the length of the wall and spaced around the outer surface of the breathing gas conduit are aligned parallel to one another and to the longitudinal axis of the breathing gas conduit. The threads 351 are supported on the helical bead 353, with the threads 351 spanning the spaces between turns of the helical bead 353. In this embodiment it is important to choose the reinforcing threads 351 (material, gauge and number) such that the threads 351 are sufficiently stiff to resist buckling under the transiently reduced internal pressures that could be expected during patient breathing. Unrestrained or excessive buckling of the threads 351 could lead to unacceptable levels of conduit axial contraction. The axial threads 351 may be a spun or braided fibres, drawn or extruded mono filaments or other equivalent forms.

The embodiment of FIG. 13 provides a breathing circuit component which may comprise all or part of a breathing circuit, reinforced against crushing by the helical bead 353 and against longitudinal extension by the axial threads 351. The spanning threads prevent direct contact between a user and the surface of the breathing circuit component, reducing the risk of punctures and the like.

When the breathing circuit component comprises an expiratory breathing gas conduit comprising, or part of, an expiratory limb of a breathing circuit, the purpose of the breathable region or regions of the conduit wall is to allow diffusion of water vapour from, for example, the expiratory limb of the breathing circuit along the path thereof independent of specific drain locations, if indeed any drain locations are provided. This eliminates the buildup of condensation within the expiratory limb by drying the humidified gases during their flow through the expiratory limb. This furthermore reduces the humidity of the gases arriving at ancillary equipment, such as filters, ventilators and the like reducing the risk of condensation accumulation, thereby improving their operation.

In accordance with a further aspect of the invention, and as exemplified in FIGS. 11 and 12, a breathing circuit component in the form of a breathing gas conduit incorporating one or more longitudinal strips of breathable membrane may further be incorporated in a coaxial breathing circuit as a passive humidification device. In particular referring to the cross section in FIG. 11 the coaxial breathing circuit may include an outer conduit 11 and an inner conduit 10. For heat transfer reasons, the inner conduit 10 carries the inspiratory flow in the space 12 there within. The expiratory flow is carried in the space 13 between the inner conduit 10 and the outer conduit 11. This airflow configuration is indicated by arrows 20, 19 respectively in FIG. 12. It will be appreciated that the opposite airflow configuration could alternatively be provided, with the arrows 19, 20 in the reverse direction. Alternatively, the inspiratory flow may be carried in the radially outermost space 13, with the expiratory flow being carried in the innermost space 12.

The inner conduit 10 is formed having either one or more longitudinal strips 6, 7 of breathable membrane in the wall 1 thereof, or alternatively the wall 1 is formed entirely of breathable membrane, as has previously been described with reference to FIGS. 9, 10 and 11. Thus humidity in the expiratory flow space 13 may pass through the sections A, B of breathable membrane to humidify the inspiratory flow in inspiratory flow space 12.

The breathable membrane works on relative partial pressures of water vapour so, with the flows in a counter flow arrangement substantial passive humidification of the inspiratory flow can be achieved.

Referring to FIG. 12 a breathing circuit configuration including the coaxial breathing gas conduit depicted in FIG. 11 is represented. In this circuit the breathing gas conduit has a patient end connector 15 and a ventilator end connector 16 having inspiratory port 17 and an expiratory port 18. The inspiratory 20 and expiratory 19 counter flows are indicated.

A sensor may be located, for example, in the patient end connector 15 to detect, for example, a short circuit indicative of a leak in the interior conduit.

In addition to the above to reduce or eliminate the formation of condensation within either the inner or outer conduit, 10 or 11 respectively, and to maintain a substantially uniform temperature in the gases flow through the breathing gas conduit, a heater means, such as a resistance heater wire, may be provided within either the inner or outer conduit, disposed within the gases spaces 12 or 13 or within the conduit walls themselves. In one possibility the heater wire may also serve as a reinforcing support (helical wire 25 in FIG. 12) within the inner conduit 10 or in the outside conduit as with the coaxial conduit.

A further breathing circuit component to which the present invention can be applied is catheter mounts. A catheter mount connects between a patient interfacing component such as a mouth piece, nasal mask or endotracheal conduit and the dual limbs of a breathing circuit. Connection with the dual limbs of the breathing circuit is generally via a wye connector. In the patient inhalation and exhalation cycle the dual limbs of the breathing circuit each have a distinct role, one as inhalation conduit and one as exhalation conduit. The catheter mount serves a dual role, transporting both inhaled and exhaled gases. Accordingly, the catheter mount can have significant disadvantages.

Figure 14:
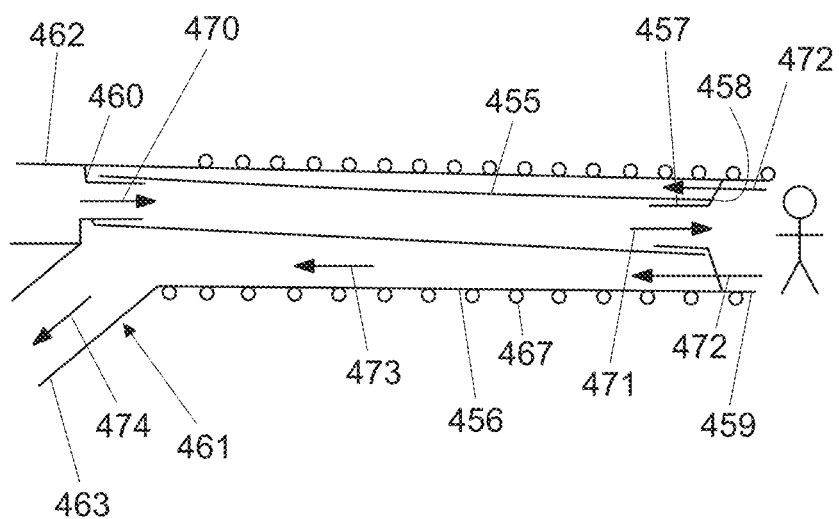
FIG. 14 is a schematic cross sectional view of a catheter mount incorporating a breathing circuit component of the present invention.

A catheter mount incorporating the present invention is depicted in FIG. 14. The catheter mount incorporates the wye connector at the ventilator end. An internal conduit 455 extends coaxially with the outer conduit 456. The internal conduit 455 is supported at its patient end on an internal conduit connector 457 which is turn is supported via support struts 458 from patient end connector 459. The inner conduit 455 is supported at its other end on an inner conduit connector 460 which forms part of the ventilator end connector 461.

In the catheter mount of FIG. 14 the ventilator end inner conduit connector 460 communicates with the inspiratory conduit connector 462. The outer conduit 456 is formed entirely from breathable material, and may also include lateral reinforcement (a spiral reinforcing bead 467) and longitudinal reinforcement (axially oriented threads 490) on the outside thereof. When constructed according to the manner earlier described with respect to FIG. 2 the spiral bead 467 is laid on the overlap between consecutive turns of the extruded tape and assists fusion of the overlap and reinforcement against crushing.

Therefore in use the catheter mount according to FIG. 14 has an inspiratory flow entering the catheter mount as indicated by arrow 470. The inspiratory flow passes through the inner conduit to exit to the patient through the patient end connector 459 as indicated by arrow 471. Upon patient exhalation, whether assisted or otherwise, expired gases pass through connector 459 and into the space surrounding the inner conduit 455 as indicated by arrows 472. These gases pass along the inside of the wall of outer conduit 456 as indicated by arrow 473 and out through the expiratory conduit connector 463 of ventilation connector 461 as indicated by arrow 474. In passing through the catheter mount within the space between the inner conduit 455 and the outer wall 456 water vapour may pass through the water vapour permeable portions of the outer conduit 456. The entire length of outer conduit 456, apart from any reinforcing rib, is breathable. In this way, although the expired gases may experience some temperature drop as they pass through the catheter mount to the expiratory conduit connector 463, hand in hand with this temperature drop is a reduction in humidity by water vapour passing through the breathable membrane of the outer conduit. Accordingly, relative humidity of the expiratory flow is reduced and rain out is reduced. A breathing circuit component, such as breathing gas conduit 1, in accordance with the invention, for example as shown with reference to FIGS. 3 to 5, stems from work which has been conducted to provide an improved breathing circuit component, and particularly, an improved breathing gas conduit of a respiratory apparatus. In an embodiment the breathing circuit component is a relatively short breathing gas conduit configured to be connected at one end to a patient interface and at the other end to an inspiratory gas conduit comprising part of a breathing circuit. The ends of the relatively short breathing gas conduit may be provided with, or comprise, connectors for connecting to the patient interface and the inspiratory gas conduit.

The breathing circuit component may comprise a breathing gas conduit configured to form any part of a breathing circuit and may therefore comprise all or part of a breathing gas inspiratory conduit delivering breathable gas to the patient from the apparatus for inhalation via a suitable patient interface, or may comprise all or part of a breathing gas expiratory conduit for delivering expiratory gas from the patient interface. The patient interface may be any interface configured to deliver breathing gas to a patient and may include any one of:

a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose;
f) a hybrid mask comprising a combination of nasal pillows/prongs and an oral seal;
i) an endotracheal conduit; and
j) a tracheostomy interface.

In other embodiments the breathing circuit component may comprise a connector or adaptor, for connection to an inspiratory or expiratory gas conduit as above. Such an adaptor may be configured to connect one end of an inspiratory or expiratory gas conduit to another component of a respiratory therapy or treatment apparatus. In an embodiment, the breathing circuit component comprises a relatively short length of breathing gas conduit connected between a patient interface at one end, and an inspiratory gas conduit at the other end.

Figure 17:
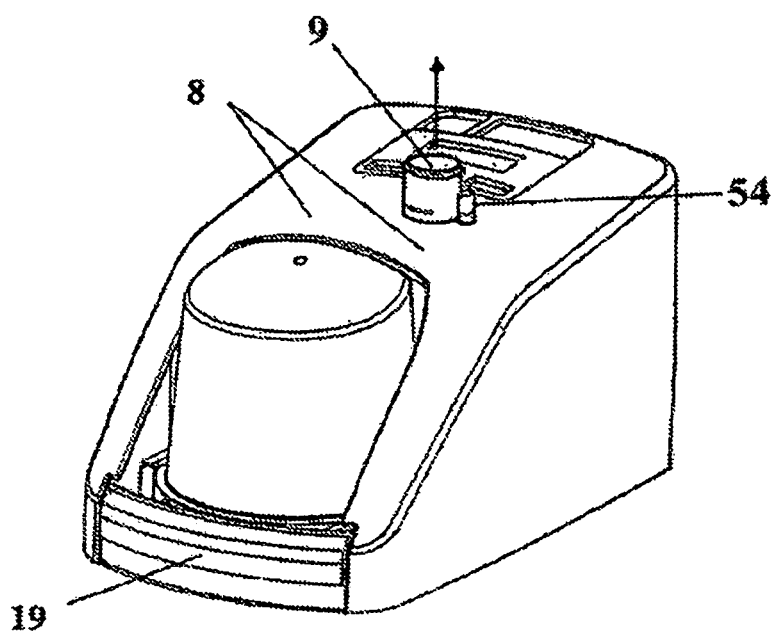
FIG. 17 is a side view of a breathing gas conduit connected between a patient interface and a blower/humidifier unit, constructed and operative in accordance with an embodiment of the present invention.

In one example, such a breathing gas conduit is connected directly between the patient interface and a blower/humidifier unit as shown in FIG. 17. The breathing gas conduit may comprise an intermediate component being a relatively short length of breathing gas conduit between a patient interface such as a nasal cannula and a conduit or conduit connector, the conduit connector being for connection to a further length of breathing gas conduit leading from a blower-humidifier unit. An example of such a blower-humidifier unit is illustrated in FIG. 17, this unit being made and sold by the applicant under the trade name AIRVO. Such a unit comprises a fan or blower configured to generate a flow of that gas. In one example, a source of oxygen may be connected to the blower unit to supplement ambient air that is pumped by the fan or blower. In another example, the fan or blower may simply draw in and pump ambient air only, without any other source of breathable gas being provided. The fan or blower is connected to a humidifier which heats water to generate water vapour which mixes with the flow of gas to humidify the gas. The humidifier typically comprises a humidifier chamber and heater plate.

With reference to the breathing gas conduit 1 of FIGS. 3 to 5, the breathing gas conduit 1 is formed of a spirally or helically wound strip of vapour permeable membrane 6 supported at overlapping edges by a spiralling supporting rib or bead 3.

The vapour permeable membrane 6 is approximately 40 microns thick and/or may fall within the range of approximately 35 to 45 microns. The vapour permeable membrane 6 may be non-porous.

Water vapour in gas contained in or flowing through the breathing gas conduit 1 permeates through voids in the membrane 6 when there is a temperature difference between the interior and exterior of the conduit 1 so that water vapour flows in the direction of the 'warm side' to the 'cold side' of the conduit 1, that is, radially outwardly from the gas flow passageway defined by the membrane 6.

The membrane 6 is such that it does not allow viruses/microorganisms to pass inwardly through the membrane 6 into the gas flow passageway inside the breathing gas conduit 1.

The membrane 6 of breathing gas conduit 1 is supported by supporting spirally wound ribs 3 which:
Are manufactured from a semi-rigid plastic.
Prevent or resist folding or crushing of the breathing gas conduit 1.
Have a pitch of approximately 4.5 mm.

In some examples a colour pigment may be added to the membrane 6 and/or ribs to colour the conduit in a desirable manner. For example, a white pigment may be added to the spiral ribs for a 'whiter', cleaner, appearance.

In another example, a length of the improved breathing gas conduit 1 as described above may be assembled with a conduit end connector at one end and a patient interface at an opposed, patient end. The conduit end connector may be connected to a further breathing gas conduit, which may or may not also be breathable and/or heated, for connection to the blower/humidifier. For example, the further breathing gas conduit may be an inspiratory gas conduit. The patient interface may comprise any suitable interface, as set out above.

The length of the breathing gas conduit may be longer than that of prior art arrangements. For example, the breathing gas conduit of the above described nasal cannula apparatus may be increased to substantially 370 mm or to a length falling within the range of approximately 360 to 380 mm, from around 320 mm in prior art arrangements. This additional length of the breathing gas conduit may improve patient fit and/or maintain substantially similar thermal performance to that of prior art conduits. The length of the improved breathing gas conduit may be adjusted to further adjust for patient fit and/or vapour permissibility of the breathing gas conduit. For example, a suitable improved breathing gas conduit length may fall within the range of approximately 310 mm to 410 mm. This may improve patient fit and/or maintain substantially similar thermal performance to that of prior art breathing gas conduits.

The increased thickness membrane is stiffer and, consequently, more self-supporting than prior art breathing gas conduits (which may be around 25 μm in some examples). As such, the membrane is less likely to tear, rupture, or be caught in machinery during spiral winding formation of the breathing gas conduit. There are therefore fewer manufacturing rejections as compared to prior art breathing gas conduits.

In use, the increased thickness of the membrane improves its strength and, consequently, its durability, and the strength and durability of the breathing gas conduit as a whole. As such, the membrane is less likely to tear, puncture or rupture when mishandled or snagged by a user or clinician or inexperienced assembler. In line with the testing as described later in the description, the increased wall thickness of the breathing gas conduit increases the longitudinal force required to break the breathing gas conduit along its longitudinal axis, and increases the lateral force required to break the breathing gas conduit substantially transverse of its longitudinal axis.

The increased thickness membrane is stiffer and, consequently produces less 'crinkle' noise when flexed or rumpled. Such a crinkle noise of prior art breathing gas conduits has proven to be disliked by patients particularly when the patient is trying to rest or sleep. Surprisingly, it has been found that a thicker membrane can be used to reduce this noise, without the extra weight or reduced flexibility of such a breathing gas conduit being objected to by patients.

In the above examples, the membrane or web is formed from breathable material of 40 μm±5 μm tolerance membrane wall thickness.

In one example, the pitch of the spiralling wound membrane and ribs forming the breathing gas conduit is approximately 4.5 mm and and/or may fall within the range of approximately 3.8 to 5.2 mm.

A breathing gas conduit 1 in accordance with the present invention may have a ratio of bead pitch to membrane wall thickness in the range of 1:0.0080 to 1:0.0128. In one embodiment of the present invention, the ratio is in the range of 1:0.0080 to 1:0.0118. In another embodiment of the present invention, the ratio is of 1:0.0088.

The above a relationship between membrane wall thickness and pitch may provide an optimum balance of at least the following characteristics:
Conduit strength (in both lateral and longitudinal directions)
'Crinkle' noise of the conduit
Conduit flexibility/rigidity
Material used in the production of the conduit
Conduit weight Vapour permissibility (particularly due to the amount of membrane exposed surface area)

It will be appreciated that the parameters of the breathing gas conduit may be adjusted to desirably vary properties of the breathing gas conduit. For example:

A greater membrane wall thickness with respect to pitch may result in:
  increased conduit strength
  decreased 'crinkle' noise
  decreased conduit flexibility
  decreased conduit vapour permissibility (due to increased membrane wall thickness)
  increased conduit weight (due to thicker membrane wall)

Conversely, a lesser membrane wall thickness with respect to pitch may result in:
  decreased strength
  increased 'crinkle' noise
  increased conduit flexibility (i.e. such that the conduit may fold on itself and/or create a flow restriction)
  increased vapour permissibility (due to decreased membrane wall thickness) decreased conduit weight (due to thinner membrane wall)

A greater pitch with respect to membrane wall thickness may result in:
  decreased conduit strength
  increased 'crinkle' noise (i.e. greater 'crinkles' are allowed to form due to the increased membrane material span between ribs)
  increased conduit flexibility (i.e. such that the conduit may fold on itself and/or create a flow restriction)
  decreased material required to form the conduit (due to increased number of spirally wound turns)
  increased vapour permissibility (due to increased surface area of the membrane exposed)
  decreased conduit weight (due to decreased material)

Conversely, a lesser pitch with respect to membrane wall thickness may result in:
  increased strength
  decreased 'crinkle' noise
  decreased conduit flexibility
  increased material required to form the conduit (due to increased number of spirally wound turns)
  increased conduit weight (due to increased material)
  decreased vapour permissibility (due to decreased surface area of the membrane exposed)

The 40 µm membrane is thicker, and consequently stiffer, than that of the prior art breathing gas conduits (typically having around a 25 micron membrane thickness). As the membrane is stiffer, the membrane may require less structural support from the spiral ribs or bead. As such, the pitch of the ribs may be increased (i.e. spread) to reduce the structural support provided by the ribs. Increasing the pitch of the ribs may subsequently advantageously require less rigid plastic material and would increase the exposed surface area of the membrane, improving conduit flexibility and/or breathability.

Conversely, the pitch of the spiral ribs or bead may be reduced to provide additional support to the conduit.

For example, a suitable conduit pitch may fall within the range of approximately 3.8 mm to 5.2 mm, and in one example may be 4.5 mm.

A breathing gas conduit 1 in accordance with the invention also exhibits significantly increased resistance to permanent deformation such that the force required to permanently deform is considerably higher than with prior art breathing gas conduits. Permanent deformation may occur across a small portion of the conduit or the complete length of the breathing gas conduit. Permanent deformation may occur as a result of catching, snagging, tugging, or the like, of the breathing gas conduit, in use or during manufacture.

Permanent deformation of the breathing gas conduit is undesirable for at least the following reasons:

Stretching further thins the membrane material, which may result in:
  Greater 'crinkle' noise
  Reduced thermal retention
  Increased risk of puncture (i.e. due to forces in the lateral direction)

Stretching also further spreads/increases the pitch of the spiral ribs, which may result in:
  Reduced support in the both the lateral and longitudinal directions
  Excess flexibility (i.e. such that the conduit may fold on itself and/or create a flow restriction)
  Reduced visual appeal of the conduit Additionally, the increased wall thickness of breathing gas conduit 1 increases the longitudinal force required to break the breathing gas conduit 1 along its longitudinal axis, and increases the lateral force required to break the breathing gas conduit 1 substantially transverse of its longitudinal axis.

It will be appreciated that one, some or all of the above breathing gas conduit properties may be varied in accordance with the invention.

An example of such a membrane as described above is a membrane sold under the brand name Sympatex. It will be appreciated that membranes of similar thicknesses produced by other manufacturers could alternatively be used after suitable investigation and experimentation is conducted with respect to such properties as vapour transmissibility, heat retention, 'crinkle' noise produced, membrane/conduit strength, and compatibility with existing production equipment.

The improved breathing gas conduit is more durable both during manufacturing and in use. As a result, the breathing gas conduit will be less susceptible to damage during manufacture and end use.

The improved breathing gas conduit also produces less 'crinkle' noise when flexed or rumpled. As a result, it is anticipated that the improved breathing gas conduit will be better received by users. It has been surprising found that despite being thicker, and therefore having all of the above properties, the breathing gas conduit still achieves a suitable level of transfer of water vapour. This is contrast to the expectation in the art that a breathing gas conduit with this significantly increased wall thickness would not pass water vapour so successfully. It is therefore an entirely unexpected outcome that the problems of noise and low durability of prior art breathing gas conduits have been solved, or at least alleviated, by making the breathing gas conduit wall thicker.

An improved breathing gas conduit in accordance with one or more embodiments of this disclosure was tested against a breathing gas conduit in accordance with the prior art, to determine average sound levels. The improved breathing gas conduit was of 40 µm membrane thickness in accordance with the present invention, while the other breathing gas conduit of the prior art dimensions was of a 25 µm membrane thickness in accordance with the prior art.

The tests were conducted on a noise testing rig, with the breathing gas conduit being fixed towards one end of the rig by a clamp, and attached to a stepper motor at the other end of the rig. Actuation of the stepper motor caused the end of the conduit attached to the stepper motor to flex towards and away from the stepper motor. The stepper motor was actuated to run forward and back 180 degrees with approximately a two second cycle time, with the entire noise testing rig placed within a sound laboratory and the noise measured. Whereby the noise was measured by way of a sound level meter and an array of microphones positioned over and around the noise testing rig. The noise created by the stepper motor itself was consistent throughout all tests. So our results show that the tube with the 40 micron membrane is quieter regardless of the stepper motor noise.

The results data of this testing is described as follows and is further shown in FIG. 15, a graph of flexible sound testing results 515 comparing decibel (dB) readings 517 of 40 μm membrane thickness conduit 518 with flexitube 25 μm membrane thickness conduit 519.

Figure 16:
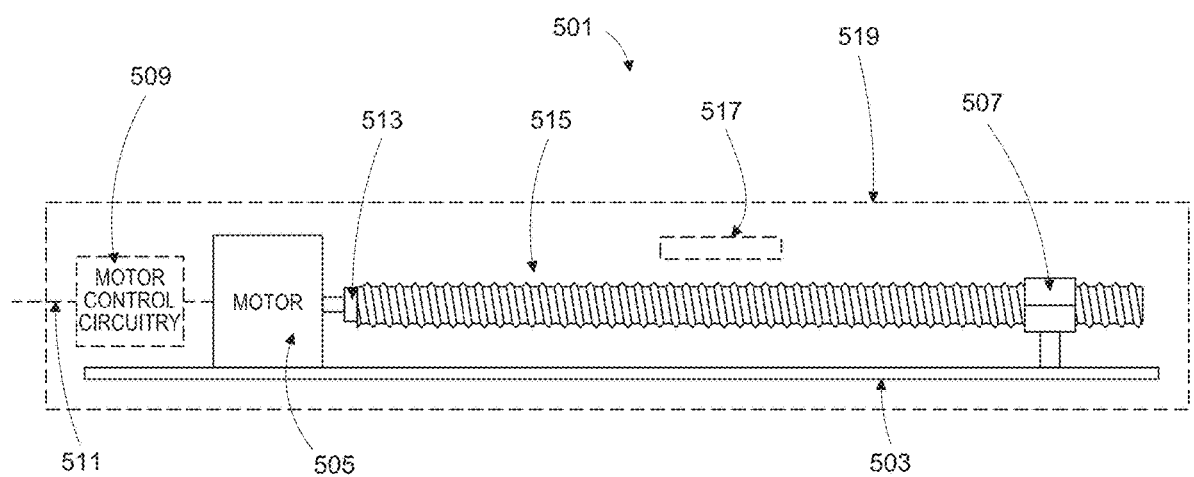
FIG. 16 is a plan view of a breathing gas conduit according to an embodiment of the present invention, mounted for testing on a sound testing rig.

FIG. 16 illustrates the noise testing rig 501 as described. The rig 501 comprises a base plate 503, with the stepper motor 505 mounted towards one end of the plate 503, and a conduit clamp 507 also mounted on the plate 503, spaced from the motor 505. Motor control circuitry 509 and a motor power supply cable 511 are also shown for completeness. A tube attachment 513 is associated with a breathing gas conduit 515 mounted on the plate 503 by the conduit clamp 507. The noise testing rig 501 is further shown placed within a sound laboratory 519 provided with a sound level measuring device 517, for example a microphone array, such as that used while testing.

Figure 15:
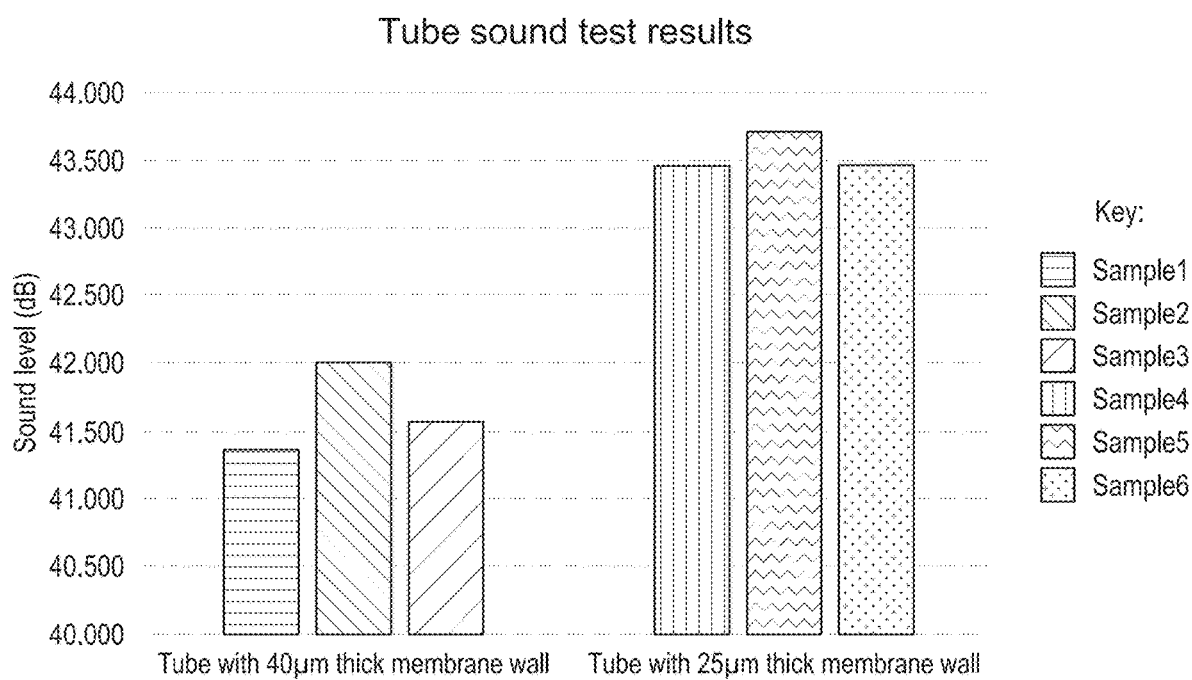
FIG. 15 is a graph displaying the results of sound testing between a breathing gas conduit constructed and operative according to an embodiment of the present invention and a breathing gas conduit known in the art.

Three conduits were tested at each membrane thickness, with each conduit being represented by a separate bar of the graph of FIG. 15. Each conduit was tested three times and the average sound level calculated over the three tests for each conduit, and subsequently for each conduit membrane thickness.

| Tube | Trial | | | Average Sound | Average Sound |
|---|---|---|---|---|---|
| Number | 1 | 2 | 3 | Level (dB) | Level (dB) |
| 40 μm membrane thickness conduit | 1 | 41.2 | 41 | 41.8 | 41.347 | 41.639 |
| | 2 | 42.7 | 41.4 | 41.8 | 42.001 | |
| | 3 | 41.7 | 41.1 | 41.8 | 41.544 | |
| 25 μm membrane thickness conduit | 1 | 43.3 | 43.6 | 43.5 | 43.468 | 43.548 |
| | 2 | 43.8 | 43.8 | 43.5 | 43.702 | |
| | 3 | 43.6 | 43.5 | 43.5 | 43.468 | |

These results affirm that a breathing gas conduit in accordance with the present disclosure exhibits significantly and unexpectedly improved properties over the prior art conduits, in particular, desirably reduced noise in use. At the least a breathing gas conduit in accordance with the present disclosure will be quieter in use and will likely be better received by users.

Although the present invention has been described in terms of certain embodiments, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

The invention claimed is:

1. A breathing gas conduit for a respiratory apparatus including:
   an inlet;
   an outlet;
   an enclosing wall defining a gases passageway between the inlet and the outlet, at least a region of the enclosing wall comprising a membrane that allows passage of water vapour without substantially allowing a passage of liquid water or respiratory gases, the membrane comprising a membrane wall thickness; and
   a bead helically wound around the enclosing wall, the bead comprising a bead pitch defined by a distance between adjacent winds of the bead,
   wherein the breathing gas conduit comprises a ratio of bead pitch to membrane wall thickness between 1:0.0080 to 1:0.0128 so as to reduce noise production when the breathing gas conduit is moved, flexed, or bent.

2. The breathing gas conduit of claim 1, wherein the ratio of bead pitch to membrane thickness is between 1:0.0080 to 1:0.0118.

3. The breathing gas conduit of claim 1, wherein the membrane wall thickness is at least 35 micrometers.

4. The breathing gas conduit of claim 1, wherein the membrane wall thickness is between 35 micrometers and 40 micrometers.

5. The breathing gas conduit of claim 1, wherein the breathing gas conduit is at least one of: an inspiratory gas conduit, an expiratory gas conduit, and a portion of a gas conduit configured to be positioned between the inspiratory gas conduit and a patient interface.

6. The breathing gas conduit of claim 1, wherein the breathing gas conduit comprises at least one of: a conduit connector, a conduit adaptor, and a catheter mount.

7. The breathing gas conduit of claim 1, wherein the breathing gas conduit comprises at least one helically wound polymer strip, the at least one helically wound polymer strip comprising the membrane, wherein respective edges of adjacent turns of the at least one helically wound polymer strip are adjoining and bonded to form the enclosing wall.

8. The breathing gas conduit of claim 1, wherein the breathing gas conduit comprises lateral reinforcement that improves crush resistance of the breathing gas conduit.

9. The breathing gas conduit of claim 8, wherein the bead provides lateral reinforcement between each turn of at least one helically wound polymer strip.

10. The breathing gas conduit of claim 1, wherein the bead pitch is between 3.5 to 5.5 millimeters.

11. The breathing gas conduit of claim 1, further comprising at least one of:
    (a) the bead comprising at least one of a width of between 1 and 3 millimeters,
    (b) the bead comprising a height of between 0.5 and 2 millimeters,
    (c) a length of the gases passageway between 310 millimeters to 410 millimeters, and
    (d) the breathing gas conduit having an inner diameter between 10 to 15 millimeters.

12. The breathing gas conduit of claim 1, wherein the enclosing wall is entirely formed by the membrane.

13. The breathing gas conduit of claim 1, wherein the breathing gas conduit is resistant to extension forces up to approximately 30 Newton in a longitudinal direction without permanent deformation.

14. The breathing gas conduit of claim 1, wherein the breathing gas conduit is resistant to an applied force up to approximately 15 Newton in a lateral direction without a breathing circuit component breaking.

15. A breathing circuit assembly including:
a patient interface; and
a breathing circuit component comprising:
an inlet,
an outlet,
an enclosing wall defining a gases passageway between the inlet and the outlet, at least a region of the enclosing wall comprising a membrane that allows passage of water vapour without substantially allowing a passage of liquid water or respiratory gases, the membrane comprising a membrane wall thickness, and
a bead helically wound around the enclosing wall, the bead comprising a bead pitch defined by a distance between adjacent winds of the bead, wherein the breathing circuit component comprises a ratio of bead pitch to membrane wall thickness between 1:0.0080 to 1:0.0128 so as to reduce noise produced by movement of the breathing circuit component when in use.

16. The breathing circuit assembly of claim 15, wherein the patient interface is any one of:
a full face mask comprising a mask frame and a cushion configured to seal around a nose and a mouth of a patient;
an oral mask comprising a mask frame and a cushion configured to seal around the mouth of the patient;
a nasal mask comprising a mask frame and a cushion configured to seal around the nose of the patient;
a nasal cannula comprising one or more prongs for insertion into one or more naris of the patient;
a nasal mask comprising one or more nasal pillows configured to seal against the nose of the patient;
a hybrid mask comprising a combination of nasal pillows/prongs and an oral seal;
an endotracheal conduit; and
a tracheostomy interface.

17. The breathing circuit assembly of claim 15, further comprising at least one of:
a lanyard configured to be attached at or adjacent a first end of the breathing circuit component;
a conduit connector configured to connect a first end of the breathing circuit component to an inspiratory gas conduit;
an inspiratory gas conduit configured to deliver inspiratory gases to the patient interface via the breathing circuit component;
a humidifier configured to humidify inspiratory gases prior to delivery of the inspiratory gases to the patient interface; and
a gases source couplable to the patient interface through the breathing circuit component.

18. A respiratory apparatus comprising:
a gas source;
an inspiratory gas conduit;
a breathing gas conduit comprising:
an inlet,
an outlet,
an enclosing wall defining a gases passageway between the inlet and the outlet, at least a region of the enclosing wall comprising a membrane that allows a passage of water vapour without substantially allowing passage of liquid water or respiratory gases, the membrane comprising a membrane wall thickness, and
a bead helically wound around the enclosing wall, the bead comprising a bead pitch defined by a distance between adjacent winds of the bead, wherein the breathing gas conduit has a ratio of bead pitch to membrane wall thickness between 1:0.0080 to 1:0.0128 so as to reduce noise production from movement of the breathing gas conduit;
a patient interface; and
a section of a gas conduit configured to be positioned between the inspiratory gas conduit and the patient interface.

19. The respiratory apparatus of claim 18, wherein the patient interface is any one of:
a full face mask comprising a mask frame and a cushion that seals around a nose and a mouth of a patient;
an oral mask comprising a mask frame and a cushion to seal that seals around the mouth of the patient;
a nasal mask comprising a mask frame and a cushion that seals around the nose of the patient;
a nasal cannula comprising one or more prongs that insert into one or more naris of the patient;
a nasal mask comprising one or more nasal pillows that seal against the nose of the patient;
a hybrid mask comprising a combination of nasal pillows/prongs and an oral seal;
an endotracheal conduit; and
a tracheostomy interface.

20. The respiratory apparatus of claim 18, further comprising at least one of:
(a) the bead comprising at least one of a width of between 1 and 3 millimeters,
(b) the bead comprising a height of between 0.5 and 2 millimeters,
(c) a length of the gases passageway between 310 millimeters to 410 millimeters, and
(d) the breathing gas conduit comprising an inner diameter between 10 to 15 millimeters.

* * * * *